(12) United States Patent
Wu et al.

(10) Patent No.: US 9,092,846 B2
(45) Date of Patent: Jul. 28, 2015

(54) DETECTING DEFECTS ON A WAFER USING DEFECT-SPECIFIC AND MULTI-CHANNEL INFORMATION

(71) Applicant: KLA-Tencor Corporation, Milpitas, CA (US)

(72) Inventors: Kenong Wu, Davis, CA (US); Lisheng Gao, Morgan Hill, CA (US); Grace Hsiu-Ling Chen, Los Gatos, CA (US); David W. Shortt, Milpitas, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/169,161

(22) Filed: Jan. 31, 2014

(65) Prior Publication Data

US 2014/0219544 A1 Aug. 7, 2014

Related U.S. Application Data

(60) Provisional application No. 61/759,949, filed on Feb. 1, 2013, provisional application No. 61/913,379, filed on Dec. 8, 2013.

(51) Int. Cl.
| | |
|---|---|
| *G06K 9/00* | (2006.01) |
| *G06T 7/00* | (2006.01) |
| *G01N 21/95* | (2006.01) |
| *H01L 21/66* | (2006.01) |

(52) U.S. Cl.
CPC ............ *G06T 7/001* (2013.01); *G01N 21/9501* (2013.01); *H01L 22/12* (2013.01); *G06T 2207/30148* (2013.01)

(58) Field of Classification Search
CPC ..... G06T 7/0008; G06T 7/001; G06T 7/0004; G06T 2207/30148; G01N 21/95607; G01N 21/9501; H04N 7/18
See application file for complete search history.

(56) References Cited

U.S. PATENT DOCUMENTS

| 3,495,269 A | 2/1970 | Mutschler et al. |
| 3,496,352 A | 2/1970 | Jugle |

(Continued)

FOREIGN PATENT DOCUMENTS

| CN | 1339140 | 3/2002 |
| CN | 1398348 | 2/2003 |

(Continued)

OTHER PUBLICATIONS

U.S. Appl. No. 60/681,095, filed May 13, 2005 by Nehmadi et al.

(Continued)

*Primary Examiner* — Amir Alavi
(74) *Attorney, Agent, or Firm* — Ann Marie Mewherter

(57) ABSTRACT

Methods and systems for detecting defects on a wafer using defect-specific and multi-channel information are provided. One method includes acquiring information for a target on a wafer. The target includes a pattern of interest (POI) formed on the wafer and a known defect of interest (DOI) occurring proximate to or in the POI. The method also includes detecting the known DOI in target candidates by identifying potential DOI locations based on images of the target candidates acquired by a first channel of an inspection system and applying one or more detection parameters to images of the potential DOI locations acquired by a second channel of the inspection system. Therefore, the image(s) used for locating potential DOI locations and the image(s) used for detecting defects can be different.

56 Claims, 8 Drawing Sheets

(56) References Cited

U.S. PATENT DOCUMENTS

| | | |
|---|---|---|
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,475,122 A | 10/1984 | Green |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,716,889 A | 2/1998 | Tsuji et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,911 A | 3/2000 | Nozaki et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,295,374 B1 | 9/2001 | Robinson et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,366,687 B1 | 4/2002 | Aloni et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,427,024 B1 * | 7/2002 | Bishop ........................ 382/149 |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |

(56) References Cited

U.S. PATENT DOCUMENTS

| | | | |
|---|---|---|---|
| 6,608,681 B2 | 8/2003 | Tanaka et al. | |
| 6,614,520 B1 | 9/2003 | Bareket et al. | |
| 6,631,511 B2 | 10/2003 | Haffner et al. | |
| 6,636,301 B1 | 10/2003 | Kvamme et al. | |
| 6,642,066 B1 | 11/2003 | Halliyal et al. | |
| 6,658,640 B2 | 12/2003 | Weed | |
| 6,665,065 B1 | 12/2003 | Phan et al. | |
| 6,670,082 B2 | 12/2003 | Liu et al. | |
| 6,680,621 B2 | 1/2004 | Savtchouk | |
| 6,691,052 B1 | 2/2004 | Maurer | |
| 6,701,004 B1 | 3/2004 | Shykind et al. | |
| 6,718,526 B1 | 4/2004 | Eldredge et al. | |
| 6,721,695 B1 | 4/2004 | Chen et al. | |
| 6,734,696 B2 | 5/2004 | Horner et al. | |
| 6,738,954 B1 | 5/2004 | Allen et al. | |
| 6,748,103 B2 | 6/2004 | Glasser et al. | |
| 6,751,519 B1 | 6/2004 | Satya et al. | |
| 6,753,954 B2 | 6/2004 | Chen | |
| 6,757,645 B2 | 6/2004 | Chang et al. | |
| 6,759,655 B2 | 7/2004 | Nara et al. | |
| 6,771,806 B1 | 8/2004 | Satya et al. | |
| 6,775,818 B2 | 8/2004 | Taravade et al. | |
| 6,777,147 B1 | 8/2004 | Fonseca et al. | |
| 6,777,676 B1 | 8/2004 | Wang et al. | |
| 6,778,695 B1 | 8/2004 | Schellenberg et al. | |
| 6,779,159 B2 | 8/2004 | Yokoyama et al. | |
| 6,784,446 B1 | 8/2004 | Phan et al. | |
| 6,788,400 B2 | 9/2004 | Chen | |
| 6,789,032 B2 | 9/2004 | Barbour et al. | |
| 6,803,554 B2 | 10/2004 | Ye et al. | |
| 6,806,456 B1 | 10/2004 | Ye et al. | |
| 6,807,503 B2 | 10/2004 | Ye et al. | |
| 6,813,572 B2 | 11/2004 | Satya et al. | |
| 6,820,028 B2 | 11/2004 | Ye et al. | |
| 6,828,542 B2 | 12/2004 | Ye et al. | |
| 6,842,225 B1 | 1/2005 | Irie et al. | |
| 6,859,746 B1 | 2/2005 | Stirton | |
| 6,879,403 B2 | 4/2005 | Freifeld | |
| 6,879,924 B2 | 4/2005 | Ye et al. | |
| 6,882,745 B2 | 4/2005 | Brankner et al. | |
| 6,884,984 B2 | 4/2005 | Ye et al. | |
| 6,886,153 B1 | 4/2005 | Bevis | |
| 6,892,156 B2 | 5/2005 | Ye et al. | |
| 6,902,855 B2 | 6/2005 | Peterson et al. | |
| 6,906,305 B2 | 6/2005 | Pease et al. | |
| 6,918,101 B1 | 7/2005 | Satya et al. | |
| 6,919,957 B2 | 7/2005 | Nikoonahad et al. | |
| 6,937,753 B1 | 8/2005 | O'Dell et al. | |
| 6,948,141 B1 | 9/2005 | Satya et al. | |
| 6,959,255 B2 | 10/2005 | Ye et al. | |
| 6,966,047 B1 | 11/2005 | Glasser | |
| 6,969,837 B2 | 11/2005 | Ye et al. | |
| 6,969,864 B2 | 11/2005 | Ye et al. | |
| 6,983,060 B1 | 1/2006 | Martinent-Catalot et al. | |
| 6,988,045 B2 | 1/2006 | Purdy | |
| 6,990,385 B1 | 1/2006 | Smith et al. | |
| 7,003,755 B2 | 2/2006 | Pang et al. | |
| 7,003,758 B2 | 2/2006 | Ye et al. | |
| 7,012,438 B1 | 3/2006 | Miller et al. | |
| 7,026,615 B2 | 4/2006 | Takane et al. | |
| 7,027,143 B1 | 4/2006 | Stokowski et al. | |
| 7,030,966 B2 | 4/2006 | Hansen | |
| 7,030,997 B2 | 4/2006 | Neureuther et al. | |
| 7,053,355 B2 | 5/2006 | Ye et al. | |
| 7,061,625 B1 | 6/2006 | Hwang et al. | |
| 7,071,833 B2 | 7/2006 | Nagano et al. | |
| 7,103,484 B1 | 9/2006 | Shi et al. | |
| 7,106,895 B1 | 9/2006 | Goldberg et al. | |
| 7,107,517 B1 | 9/2006 | Suzuki et al. | |
| 7,107,571 B2 | 9/2006 | Chang et al. | |
| 7,111,277 B2 | 9/2006 | Ye et al. | |
| 7,114,143 B2 | 9/2006 | Hanson et al. | |
| 7,114,145 B2 | 9/2006 | Ye et al. | |
| 7,117,477 B2 | 10/2006 | Ye et al. | |
| 7,117,478 B2 | 10/2006 | Ye et al. | |
| 7,120,285 B1 | 10/2006 | Spence | |
| 7,120,895 B2 | 10/2006 | Ye et al. | |
| 7,123,356 B1 | 10/2006 | Stokowski et al. | |
| 7,124,386 B2 | 10/2006 | Smith et al. | |
| 7,133,548 B2 | 11/2006 | Kenan et al. | |
| 7,135,344 B2 | 11/2006 | Nehmadi et al. | |
| 7,136,143 B2 | 11/2006 | Smith | |
| 7,152,215 B2 | 12/2006 | Smith et al. | |
| 7,162,071 B2 | 1/2007 | Hung et al. | |
| 7,170,593 B2 | 1/2007 | Honda et al. | |
| 7,171,334 B2 | 1/2007 | Gassner | |
| 7,174,520 B2 | 2/2007 | White et al. | |
| 7,194,709 B2 | 3/2007 | Brankner | |
| 7,207,017 B1 | 4/2007 | Tabery et al. | |
| 7,231,628 B2 | 6/2007 | Pack et al. | |
| 7,236,847 B2 | 6/2007 | Marella | |
| 7,271,891 B1 | 9/2007 | Xiong et al. | |
| 7,379,175 B1 | 5/2008 | Stokowski et al. | |
| 7,383,156 B2 | 6/2008 | Matsusita et al. | |
| 7,386,839 B1 | 6/2008 | Golender et al. | |
| 7,388,979 B2 | 6/2008 | Sakai et al. | |
| 7,418,124 B2 | 8/2008 | Peterson et al. | |
| 7,424,145 B2 | 9/2008 | Horie et al. | |
| 7,440,093 B1 | 10/2008 | Xiong et al. | |
| 7,570,796 B2 | 8/2009 | Zafar et al. | |
| 7,676,077 B2 | 3/2010 | Kulkarni et al. | |
| 7,683,319 B2 | 3/2010 | Makino et al. | |
| 7,738,093 B2 | 6/2010 | Alles et al. | |
| 7,739,064 B1 | 6/2010 | Ryker et al. | |
| 7,752,584 B2 | 7/2010 | Yang | |
| 7,760,929 B2 | 7/2010 | Orbon et al. | |
| 7,769,225 B2 | 8/2010 | Kekare et al. | |
| 7,774,153 B1 | 8/2010 | Smith | |
| 7,877,722 B2 | 1/2011 | Duffy et al. | |
| 7,890,917 B1 | 2/2011 | Young et al. | |
| 7,904,845 B2 | 3/2011 | Fouquet et al. | |
| 7,968,859 B2 | 6/2011 | Young et al. | |
| 8,041,103 B2 | 10/2011 | Kulkarni et al. | |
| 8,041,106 B2 * | 10/2011 | Pak et al. | 382/149 |
| 8,073,240 B2 | 12/2011 | Fischer et al. | |
| 8,112,241 B2 | 2/2012 | Xiong | |
| 8,126,255 B2 * | 2/2012 | Bhaskar et al. | 382/141 |
| 8,204,297 B1 | 6/2012 | Xiong et al. | |
| 8,269,960 B2 * | 9/2012 | Reich et al. | 356/237.5 |
| 8,775,101 B2 * | 7/2014 | Huang et al. | 702/40 |
| 2001/0017694 A1 | 8/2001 | Oomori et al. | |
| 2001/0019625 A1 | 9/2001 | Kenan et al. | |
| 2001/0022858 A1 | 9/2001 | Komiya et al. | |
| 2001/0043735 A1 | 11/2001 | Smargiassi et al. | |
| 2002/0010560 A1 | 1/2002 | Balachandran | |
| 2002/0019729 A1 | 2/2002 | Chang et al. | |
| 2002/0026626 A1 | 2/2002 | Randall et al. | |
| 2002/0033449 A1 | 3/2002 | Nakasuji et al. | |
| 2002/0035461 A1 | 3/2002 | Chang et al. | |
| 2002/0035641 A1 | 3/2002 | Kurose et al. | |
| 2002/0035717 A1 | 3/2002 | Matsuoka | |
| 2002/0054291 A1 | 5/2002 | Tsai et al. | |
| 2002/0088951 A1 | 7/2002 | Chen | |
| 2002/0090746 A1 | 7/2002 | Xu et al. | |
| 2002/0134936 A1 | 9/2002 | Matsui et al. | |
| 2002/0144230 A1 | 10/2002 | Rittman | |
| 2002/0145734 A1 | 10/2002 | Watkins et al. | |
| 2002/0164065 A1 | 11/2002 | Cai et al. | |
| 2002/0168099 A1 | 11/2002 | Noy | |
| 2002/0176096 A1 | 11/2002 | Sentoku et al. | |
| 2002/0181756 A1 | 12/2002 | Shibuya et al. | |
| 2002/0186878 A1 | 12/2002 | Hoon et al. | |
| 2002/0192578 A1 | 12/2002 | Tanaka et al. | |
| 2003/0004699 A1 | 1/2003 | Choi et al. | |
| 2003/0014146 A1 | 1/2003 | Fujii et al. | |
| 2003/0017664 A1 | 1/2003 | Pnueli et al. | |
| 2003/0022401 A1 | 1/2003 | Hamamatsu et al. | |
| 2003/0033046 A1 | 2/2003 | Yoshitake et al. | |
| 2003/0048458 A1 | 3/2003 | Mieher et al. | |
| 2003/0048939 A1 | 3/2003 | Lehman | |
| 2003/0057971 A1 | 3/2003 | Nishiyama et al. | |
| 2003/0076989 A1 | 4/2003 | Maayah et al. | |
| 2003/0086081 A1 | 5/2003 | Lehman | |
| 2003/0094572 A1 | 5/2003 | Matsui et al. | |

(56) References Cited

U.S. PATENT DOCUMENTS

| | | |
|---|---|---|
| 2003/0098805 A1 | 5/2003 | Bizjak |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1 | 12/2007 | Zafar et al. |
| 2008/0013083 A1 | 1/2008 | Kirk et al. |
| 2008/0015802 A1 | 1/2008 | Urano et al. |
| 2008/0016481 A1 | 1/2008 | Matsuoka et al. |
| 2008/0018887 A1 | 1/2008 | Chen et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0067703 A1 | 3/2009 | Lin et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2009/0299681 A1 | 12/2009 | Chen et al. |
| 2009/0323052 A1 | 12/2009 | Silberstein et al. |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2010/0188657 A1 | 7/2010 | Chen et al. |
| 2010/0226562 A1 | 9/2010 | Wu et al. |
| 2011/0013825 A1 | 1/2011 | Shibuya et al. |
| 2011/0052040 A1 | 3/2011 | Kuan |
| 2011/0184662 A1 | 7/2011 | Badger et al. |
| 2011/0251713 A1 | 10/2011 | Teshima et al. |
| 2011/0276935 A1 | 11/2011 | Fouquet et al. |
| 2011/0311126 A1 | 12/2011 | Sakai et al. |
| 2011/0320149 A1* | 12/2011 | Lee et al. ................ 702/83 |
| 2012/0308112 A1 | 12/2012 | Hu et al. |
| 2012/0319246 A1 | 12/2012 | Tan et al. |
| 2013/0009989 A1 | 1/2013 | Chen et al. |
| 2013/0027196 A1 | 1/2013 | Yankun et al. |
| 2014/0050389 A1* | 2/2014 | Mahadevan et al. ........ 382/149 |
| 2014/0185919 A1* | 7/2014 | Lang et al. ............... 382/149 |
| 2014/0193065 A1* | 7/2014 | Chu et al. ................ 382/149 |
| 2014/0219544 A1* | 8/2014 | Wu et al. ................. 382/149 |

FOREIGN PATENT DOCUMENTS

| | | |
|---|---|---|
| CN | 1646896 | 7/2005 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |

(56) References Cited

FOREIGN PATENT DOCUMENTS

| | | |
|---|---|---|
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2007-234798 | 9/2007 |
| JP | 2009-122046 | 6/2009 |
| JP | 2010-256242 | 11/2010 |
| JP | 2012-225768 | 11/2012 |
| KR | 10-2001-007394 | 1/2001 |
| KR | 10-2001-0037026 | 5/2001 |
| KR | 10-2001-0101697 | 11/2001 |
| KR | 10-2003-0055848 | 7/2003 |
| KR | 10-2006-0075691 | 7/2005 |
| KR | 10-2005-0092053 | 9/2005 |
| KR | 10-2006-0124514 | 12/2006 |
| KR | 10-0696276 | 3/2007 |
| KR | 10-2010-0061018 | 6/2010 |
| KR | 10-2012-0068128 | 6/2012 |
| WO | 98/57358 | 12/1998 |
| WO | 99/22310 | 5/1999 |
| WO | 99/25004 | 5/1999 |
| WO | 99/59200 | 5/1999 |
| WO | 99/38002 | 7/1999 |
| WO | 99/41434 | 8/1999 |
| WO | 00/03234 | 1/2000 |
| WO | 00/36525 | 6/2000 |
| WO | 00/55799 | 9/2000 |
| WO | 00/68884 | 11/2000 |
| WO | 00/70332 | 11/2000 |
| WO | 01/09566 | 2/2001 |
| WO | 01/40145 | 6/2001 |
| WO | 03/104921 | 12/2003 |
| WO | 2004/027684 | 4/2004 |
| WO | 2004/097903 | 11/2004 |
| WO | 2006/012388 | 2/2006 |
| WO | 2006/063268 | 6/2006 |
| WO | 2009/152046 | 9/2009 |
| WO | 2010/093733 | 8/2010 |

OTHER PUBLICATIONS

U.S. Appl. No. 60/684,360, filed May 24, 2005 by Nehmadi et al.
U.S. Appl. No. 13/652,377, filed Oct. 15, 2012 by Wu et al.
Allan et al., "Critical Area Extraction for Soft Fault Estimation," IEEE Transactions on Semiconductor Manufacturing, vol. 11, No. 1, Feb. 1998.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automoated Defect Severity Scoring," Proceedings of the SPIE, vol. 4409, Jan. 2001, pp. 467-478.
Comizzoli, "Uses of Corona Discharges in the Semiconductor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and production metrology of thin transistor gate oxide films," Materials Science in Semiconductor Processing 2, 1999, pp. 103-147.
Dirksen et al., "Impact of high order aberrations on the performance of the aberration monitor," Proc. of SPIE vol. 4000, Mar. 2000, pp. 9-17.
Dirksen et al., "Novel aberration monitor for optical lithography," Proc. of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Huang et al., "Using Design Based Binning to Improve Defect Excursion Control for 45nm Production," IEEE, International Symposium on Semiconductor Manufacturing, Oct. 2007, pp. 1-3.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 μm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.
Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.
Numerical Recipes in C. The Art of Scientific Computing, 2nd Ed., © Cambridge University Press 1988, 1992, p. 683.
O'Gorman et al., "Subpixel Registration Using a Concentric Ring Fiducial," Proceedings of the International Conference on Pattern Recognition, vol. ii, Jun. 16, 1990, pp. 249-253.
Otsu, "A Threshold Selection Method from Gray-Level Histograms," IEEE Transactions on Systems, Man, and Cybernetics, vol. SMC-9, No. 1, Jan. 1979, pp. 62-66.
Pang et al., "Simulation-based Defect Printability Analysis on Alternating Phase Shifting Masks for 193 nm Lithography," Proceedings of SPIE, vol. 4889, 2002, pp. 947-954.
Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.
Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

(56) References Cited

OTHER PUBLICATIONS

Sahouria et al., "Full-chip Process Simulation for Silicon DRC," Mentor Graphics, Mar. 2000, 6 pages.
Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.
Schroder et al., Corona-Oxide-Semiconductor Device Characterization, 1998, Solid-State Electronics, vol. 42, No. 4, pp. 505-512.
Schroder, "Surface voltage and surface photovoltage: history, theory and applications," Measurement Science and Technology, vol. 12, 2001, pp. R16-R31.
Schroder, Contactless Surface Charge Semiconductor Characterization, Apr. 2002, Materials Science and Engineering B, vol. 91-92, pp. 196-228.
Schurz et al., "Simulation Study of Reticle Enhancement Technology Applications for 157 nm Lithography," SPIE vol. 4562, 2002, pp. 902-913.
Svidenko et al. "Dynamic Defect-Limited Yield Prediction by Criticality Factor," ISSM Paper: YE-O-157, 2007.
Tang et al., "Analyzing Volume Diagnosis Results with Statistical Learning for Yield Improvement" 12th IEEE European Test Symposium, Freiburg 2007, IEEE European, May 20-24, 2007, pp. 145-150.
Verkuil et al., "A Contactless Alternative to MOS Charge Measurements by Means of a Corona-Oxide-Semiconductor (COS) Technique," Electrochem. Soc. Extended Abstracts, 1988, vol. 88-1, No. 169, pp. 261-262.
Verkuil, "Rapid Contactless Method for Measuring Fixed Oxide Charge Associated with Silicon Processing," IBM Technical Disclosure Bulletin, vol. 24, No. 6, 1981, pp. 3048-3053.
Volk et al. "Investigation of Reticle Defect Formation at DUV Lithography," 2002, BACUS Symposium on Photomask Technology..
Volk et al. "Investigation of Reticle Defect Formation at DUV Lithography," 2003, IEEE/SEMI Advanced Manufacturing Conference, pp. 29-35.
Volk et al., "Investigation of Smart Inspection of Critical Layer Reticles using Additional Designer Data to Determine Defect Significance," Proceedings of SPIE vol. 5256, 2003, pp. 489-499.
Weinberg, "Tunneling of Electrons from Si into Thermally Grown $SiO2$," Solid-State Electronics, 1977, vol. 20, pp. 11-18.
Weinzierl et al., "Non-Contact Corona-Based Process Control Measurements: Where We've Been, Where We're Headed," Electrochemical Society Proceedings, Oct. 1999, vol. 99-16, pp. 342-350.
Yan et al., "Printability of Pellicle Defects in DUV 0.5 um Lithography," SPIE vol. 1604, 1991, pp. 106-117.
Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.
Liu, "Robust Image Segmentation Using Local Median," Proceedings of the 3rd Canadian Conference on Computer and Robot Vision (CRV'06) 0/7695-2542-3/06, 2006 IEEE, 7 pages total.
International Search Report and Written Opinion for PCT/US2014/014188 mailed May 23, 2014.

\* cited by examiner

DETECTING DEFECTS ON A WAFER USING DEFECT-SPECIFIC AND MULTI-CHANNEL INFORMATION

This application claims benefit of 61/759,949 filed Feb. 1, 2013 and claims benefit of 61/913,379 filed Dec. 8, 2013.

BACKGROUND OF THE INVENTION

1. Field of the Invention

This invention generally relates to detecting defects on a wafer using defect-specific and multi-channel information.

2. Description of the Related Art

The following description and examples are not admitted to be prior art by virtue of their inclusion in this section.

Inspection processes are used at various steps during a semiconductor manufacturing, process to detect defects on wafers. One important goal for any wafer inspection system is to suppress nuisance defects. Nuisance defects are detected events which may not be relevant to semiconductor yields. Nuisance defects may be caused by wafer noise and system noise or are physical objects on the wafer. Nuisance defects may appear anywhere on a wafer. In contrast, some defects of interest (DOI) may appear at only certain locations on a wafer.

Context information for a DOI may be used as prior knowledge for defect detection. Several approaches that use context information have been developed to detect defects. One such approach uses graphical data stream (GDS) data or design information to find hot spots where defects may occur at a higher probability and to inspect defects around the hot spots. Another such approach matches defect background and keeps or removes matched defects after defect detection.

There are, however, a number of disadvantages to such approaches. For example, the first approach works with GDS data. However, GDS information may not be available in all circumstances such as for defect engineers in semiconductor fabrication plants. In addition, the user may need software that is separated from inspection software to find the defect areas. Furthermore, the user needs to do pixel-to-design alignment (PDA) and run-time swath-based alignment to overlap care areas accurately on the images. Since a swath image which covers the entire die is very large, image distortion may cause alignment inaccuracies. If swath-based alignment fails, the locations covered by the swaths will not be inspected.

The second approach, which is performed after defect detection, can significantly slow down inspection if the defect count and types of nuisance defects are relatively large. In addition, if the defect signal is relatively weak, huge amounts of nuisance defects may be detected. The defect signal may be defined as the maximum gray-level difference between an image with a defect and a reference image without the defect. The reference image is spatially-aligned with the defect image and may be acquired from neighboring dies or from multiple dies on the wafer. Furthermore, if the methods are performed for keeping systematic DOIs, other nuisance removal mechanisms are needed to separate nuisance defects and randomly-distributed DOIs.

None of these approaches use defect-specific information and a multi-channel system with multiple optics modes to acquire wafer and defect information.

Accordingly, it would be advantageous to develop methods and/or systems for detecting defects on wafers that do not have one or more of the disadvantages described above.

SUMMARY OF THE INVENTION

The following description of various embodiments is not to be construed in any way as limiting the subject matter of the appended claims.

One embodiment relates to a computer-implemented method for detecting defects on a wafer using defect-specific information. The method includes acquiring information for a target on a wafer. The target includes a pattern of interest (POI) formed on the wafer and a known defect of interest (DOI) occurring proximate to or in the POI. The information includes a first image of the POI on the wafer acquired by imaging the POI on the wafer with a first channel of an inspection system, a second image of the known DOI on the wafer acquired by imaging the known DOI with a second channel of the inspection system, a location of the POI on the wafer, a location of the known DOI relative to the POI, and one or more characteristics computed from the POI and the known DOI.

The method also includes searching for target candidates that match the POI in a die on the wafer or on another wafer. The target candidates include the POI. POI search may be performed in a setup step prior to defect detection. After POI search, micro care areas (MCAs) may be created based on the position of the known defect relative to the POI position for each potential defect location. These locations may be provided for defect detection. In addition, the method includes detecting the known DOI in the target candidates by identifying potential DOI locations based on images of the target candidates acquired by the first channel and applying one or more detection parameters to images acquired by the second channel of the potential DOI locations. Detecting the known DOI is performed using a computer system.

There are several differences between this method and currently used context-based inspection. First, this method does not rely on graphical data stream (GDS) data. In addition, a highly accurate care area alignment may be performed to detect specific defects. The care area alignment is not performed at the swath image level. It is performed in the frame image which is the basic image element for detect detection. Furthermore, context and defect-specific information is used during setup and defect detection, not after defect detection. In addition, a multi-channel inspection system can separate POI search and defect detection using different image modes. A different image mode can be obtained by changing spectrum, aperture, polarization, and focus offset. Some image modes may be good for pattern search but may not be good in sensing the defects. On the other hand, some image modes may be good for sensing the defect but do not have a good resolution for wafer patterns. The system described herein decouples the pattern search sensitivity and defect detection sensitivity.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a wafer. The system includes an inspection subsystem configured to acquire information for a target on a wafer. The target includes a POI formed on the wafer and a known DOI occurring proximate to or in the POI. The information includes a first image of the POI on the wafer acquired by imaging the POI on the wafer with a first channel of the inspection subsystem and a second image of the known DOI on the wafer acquired by imaging the known DOI with a second channel of the inspection subsystem. The inspection subsystem is also configured to search for target candidates that match the POI on the wafer or on another wafer and to acquire images of the target candidates. The target candidates include the POI. In addition, the system includes a computer system configured to detect the known DOI in the target candidates by identifying potential DOI locations based on images of the target candidates acquired by the first channel and applying one or more detection parameters to images acquired by the second channel of the potential DOI locations. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
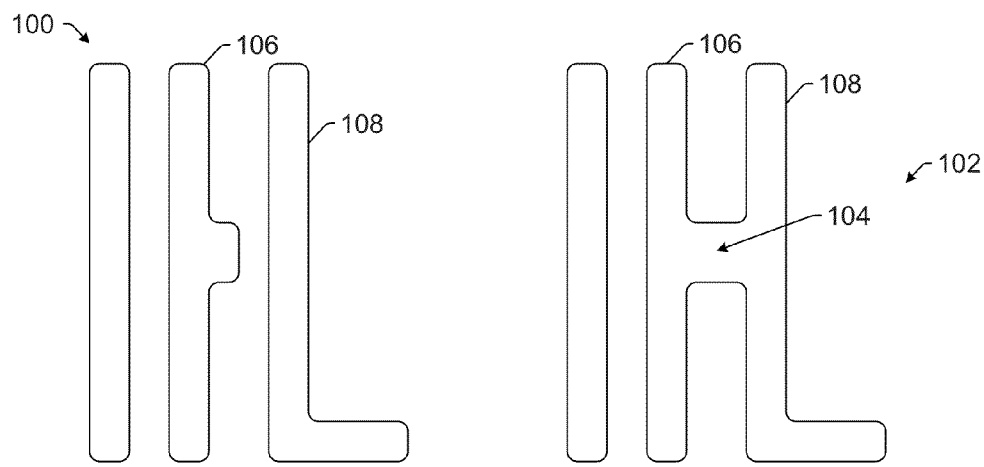
FIG. 1 is a schematic diagram illustrating a plan view of one embodiment of a pattern formed on a wafer and the pattern with a known defect of interest (DOI) detected in the pattern.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a computer-implemented method for detecting defects on a wafer. The embodiments described herein generally include two parts: 1) set up, which may include template and care area (CA) set up, and 2) defect detection. During set up, target information is collected for known defect of interest (DOI) locations and/or vulnerable locations on a wafer. During defect detection, a wafer is inspected using the target information. As will be described further herein, the embodiments apply to both multi-channel and multi-mode inspection as well as dark field (DF) and any other type of inspection.

The method includes acquiring information for a target on a wafer. The target includes a pattern of interest (POI) formed on the wafer and a known DOI occurring proximate to (near) or in the POI. The information for the target includes a first image of the POI on the wafer acquired by imaging the POI on the wafer with a first channel of an inspection system, a second image of the known DOI on the wafer acquired by imaging the known DOI with a second channel of the inspection system, a location of the POI on the wafer, a location of the known DOI relative to the POI, and one or more characteristics computed from the POI and the known DOI. Therefore, the information for the target may include information acquired with multiple channels (i.e., at least first and second channels) of an inspection system. As will be described further herein, the embodiments are particularly suitable for inspection systems that have multiple channels and uniquely leverage the multi-channel capability of such inspection systems. The inspection system may be further configured as described herein.

Given the target information (sample DOIs in specific context), the embodiments described herein may be used to detect all DOIs and suppress nuisance defects on the whole wafer. In addition, since the embodiments described herein are designed to detect defects in only target candidates containing certain patterns, the embodiments described herein are particularly useful for detecting systematic defects on wafers, which are defects that occur repeatedly in certain patterns on wafers generally due to interactions between the pattern and the process used to form the pattern on the wafer. Therefore, the DOIs may include defects in the patterns formed on the wafer such as bridges.

The POI may include only a few patterned features in the entire design for dies formed (or to be formed) on the wafer. In other words, the POI included in the target does not include the entire pattern for a die formed or to be formed on the wafer.

The information for the target may also include a location where the DOI may occur, and the location may be known and unique to the POI location. In this manner, the location of the known DOI is unique relative to the location of the POI. In other words, the POI preferably has a unique spatial relationship with a potential defect location.

In an embodiment, the location of the known DOI is obtained based on design data for the wafer. For example, defect locations and vulnerable locations can be obtained from semiconductor design files. In one such example, in set up, the target locations can come from design files through rule-based or pattern-based search.

In one embodiment, acquiring the information for the target includes importing locations of DOI samples. In another embodiment, the location of the known DOI and/or vulnerable locations on the wafer are obtained based on optical images or SEM images of the wafer. The sources of these locations may be obtained from inspection results and SEM review results. In this manner, samples of DOI may also be known from certain sources much as e-beam inspection or scanning electron microscopy (SEM) review performed on the wafer.

These locations may be used for grabbing images of the targets. For example, in set up, an image patch (template) is created for each detect type. The location of the image patch is obtained based on the defect location or the vulnerable locations. In set up, SEM images can be correlated to optical images to identity defect locations in the optical images. In addition, in set up, optical patch images included in previous inspection results can be used as the target templates or used to search for exact defect locations. For example, in one embodiment, the method includes determining the location of the known DOI in an optical image of the wafer by correlating a SEM image of the known DOI to the optical image of the wafer. In some such instances, the user will want to know the number of these kinds of defects on the whole wafer.

The information for the target may be generated during setup and may include identifying potential defect locations and computing defect information using test and reference images of sample defects. In one such embodiment, as shown in FIG. 1, pattern 100 may be formed on a wafer and is shown in FIG. 1 as it might be imaged by a high-resolution inspection system such as an e-beam inspection system or an optical inspection system. The system may grab two images, one from the target location and the other from a die or wafer on which a POI search will be performed. The features shown in pattern 100 may be included in a target described herein since as shown in pattern 102, which is equivalent to pattern 100 but with a defect occurring therein, DOI 104 such as a bridging defect between patterned feature 106 and patterned feature 108 may have been detected in one or more instances of the pattern on a wafer. The patterns shown in FIG. 1 are not intended to represent any pattern that may actually be formed on a wafer. Instead, the patterns are intended to show what types of features may be included in the POI of the targets and the types of DOI that may occur therein. The number of patterned features included in the POI may be selected such that target candidates can be identified in images acquired for the wafer or other wafers with a predetermined accuracy. The size of the POI may be also determined as described further herein.

In one embodiment, acquiring the information for the target includes displaying high-resolution images of DOI locations. The images may be generated from other systems such as SEM review machines or e-beam inspection machines. A "high-resolution" image, as that term is used herein, is defined as any image acquired at a resolution higher than that normally used for wafer inspection. In addition, acquiring the information for the target may include providing a graphics user interface (GUI) to a user. The GUI may display any of the information that is acquired for the target.

In one embodiment, acquiring the information for the target includes grabbing the image of the target on the wafer in known locations of DOI using an inspection system. For example, during setup, the system grabs two sets of images, one from the target location in a die and the other from a die on which POI search will be performed. The set of images at the target location includes test and reference images. The system aligns one image to another and computes the difference of the two images. The user manually marks the DOI location and POI location by referencing to the test or difference image. The other set of images includes the test and reference images at the corresponding location in the die for POI search. The system automatically locates the POI location in the image of the die for POI search by correlating two reference images. A template, an image of the POI, may be grabbed from the die for POI search when the user specifies the POI location.

Figure 4:
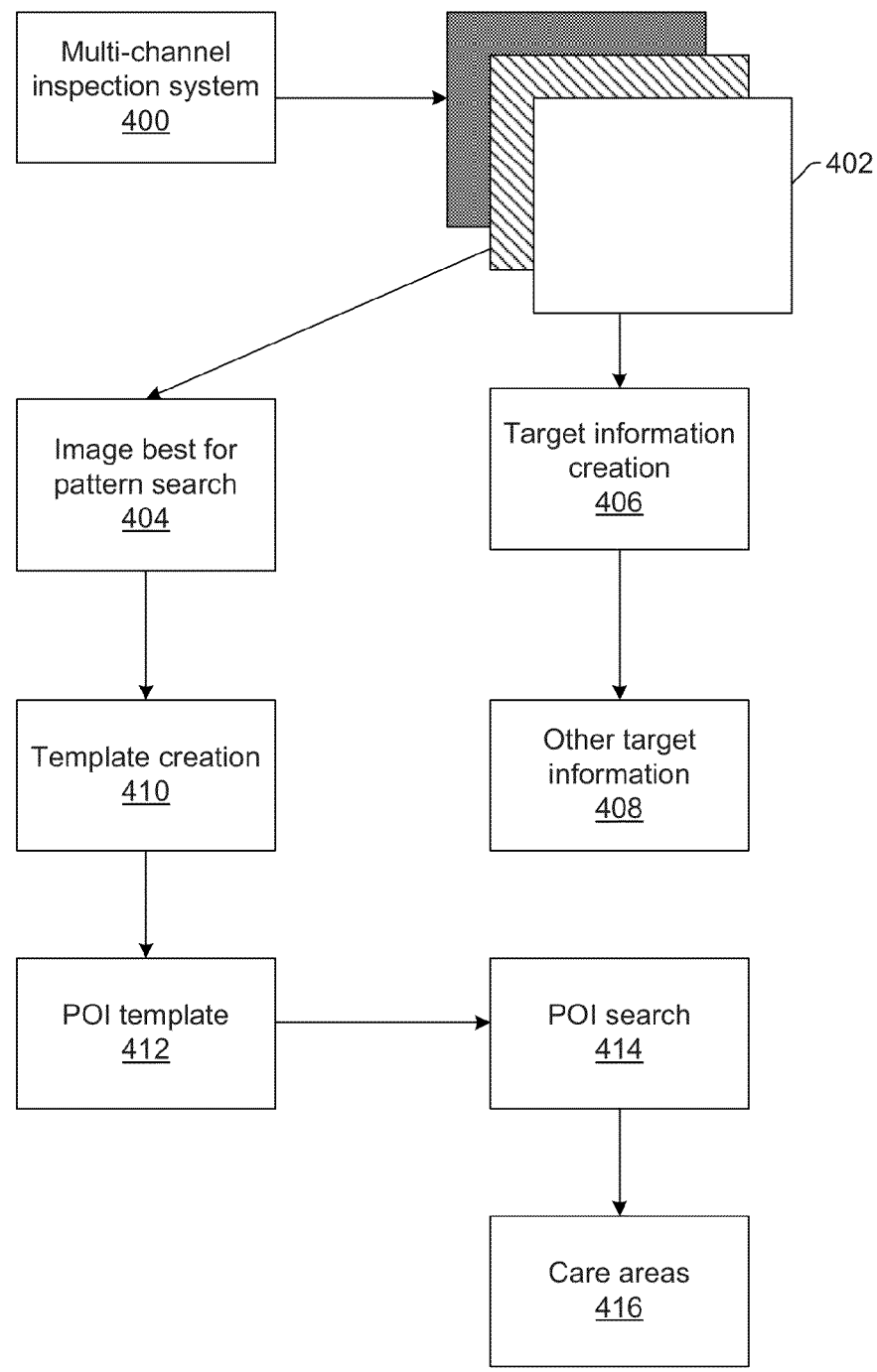
FIG. 4 is a flow chart illustrating one embodiment of a method for template and care area setup.

In another embodiment, acquiring the information for the target includes grabbing images of the target on the wafer using multiple channels of the inspection system, and the multiple channels include at least the first channel and the second channel. In this manner, the information for the target may be acquired, at least in part, by using a multi-channel inspection system. For example, as shown in the method of FIG. 4, multi-channel inspection system 400 may be used to grab multiple images 402 of the target on the wafer. In addition, multiple images may be acquired for both the POI and the known locations of the DOI and included in the information for the target. For example, the information for the target may include multiple images for the POI grabbed using multiple channels of the inspection system.

Grabbing the images may be performed in any suitable manner (e.g., scanning over the locations of the POI and the known locations of the DOI and acquiring images of the locations during the scanning). Grabbing the images of the target on the wafer may be performed using an inspection system such as that described further herein, which has the capability of acquiring a set of multiple types of wafer images of the same location through multiple channels simultaneously or sequentially. In one embodiment, the inspection system uses different optics modes in the first and second channels, and the different optics modes are defined by spectrum, aperture, polarization, scan speed, or some combination thereof. For example, a multi-channel inspection system may be used to acquire multiple images of the same location through more than one channel simultaneously or sequentially with different perspectives, spectrums, apertures, polarizations, imaging mechanisms, or some combination thereof. Among these images, some images may be relatively good for pattern resolution while other images may be relatively good for defect detection. In any case, the images can be aligned to one another by either hardware or software. For example, in one embodiment, the images acquired by the first and second channels are spatially registered to each other by image sensor calibration and alignment algorithms applied on the images, which may be performed in any suitable manner.

The images included in the target information may also include images grabbed by the inspection system and/or grabbed images that have been manipulated in some manner. For example, the first image of the POI may be acquired by imaging the POI on the wafer with one or more of the multiple channels of the inspection system and then processing the grabbed images, e.g., to generate difference images that are used as the first image(s) or to create templates from the grabbed images that are used as the first image(s), etc. In one embodiment, the method includes creating a template for the POI and modifying the template by changing the size of the template or flipping, rotating, or processing the template. The template shape may be a square or rectangle and its size may be smaller than the image acquired by an inspection system.

In another embodiment, acquiring the information for the target includes grabbing images of the POI with multiple channels of the inspection system, determining which of the grabbed images is best for pattern searching, and designating one of the multiple channels with which the best of the grabbed images for the pattern searching was grabbed as the first channel. For example, as shown in the method of FIG. 4, multiple images 402 may be used to determine image 404 that is the best for pattern search. In addition, during set up, the method may include searching the potential defect locations using one or more image types, which have the best image resolution among all images acquired. These image types may be different from the image types used for defect detection.

In some embodiments, acquiring the information for the target includes generating additional images of the wafer at and proximate to the known DOI with multiple channels of the inspection system, determining which of the additional images is best for pattern searching, and selecting the POI from the additional image that is determined to be the best for the pattern searching. For example, during set up, multiple image patches may be acquired at or near sample defect locations from one die. As shown in the method of FIG. 4, image 404 that is the best for pattern search may be used to identify a suitable POI from the patterns on the wafer that are included in that image. In some instances, the user may define the POI in the image that has the best resolution for pattern search.

In one embodiment, acquiring the information for the target includes determining a similarity between a template for the POI and an image of the target acquired by imaging the target on the wafer with the first channel and determining a uniqueness of the POI relative to other patterns proximate to the POI (i.e., the uniqueness of the POI with respect to its surroundings). For example, during template grabbing, a correlation value between images from the target die and the die for POI search may be calculated and saved for POI search. The template is selected to find the DOI location uniquely. A metric that measures uniqueness of the template may be calculated. For example, the ratio of the second highest peak and the highest peak values among correlation values for all locations in the image can be used as the uniqueness metric. The user can adjust the template location according to the uniqueness value.

Figure 2:
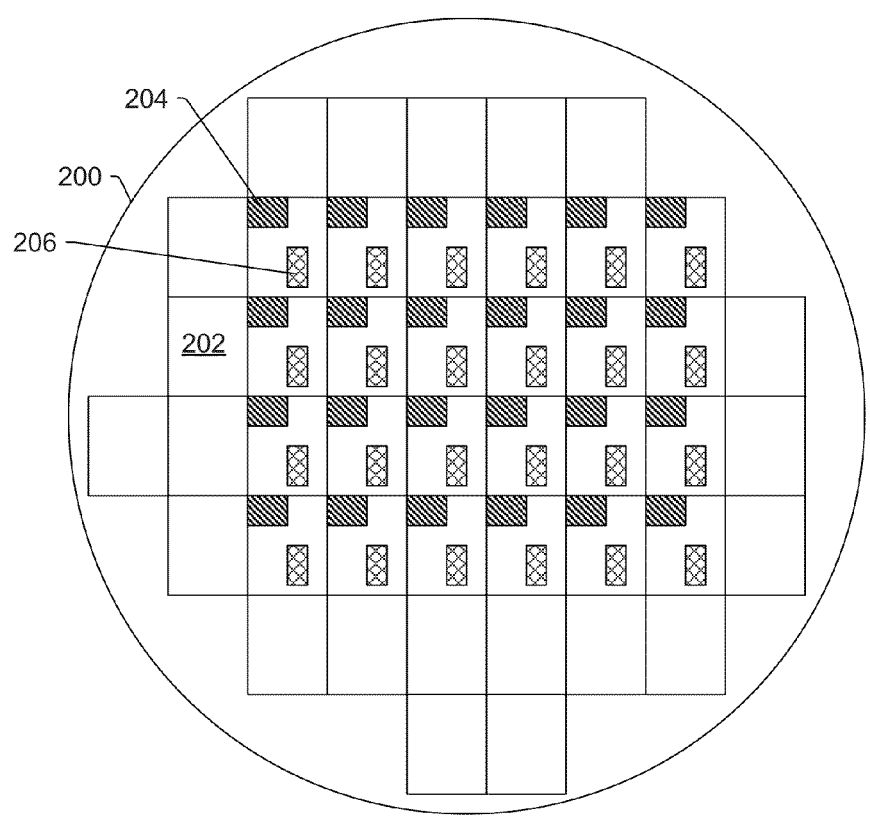
FIG. 2 is a schematic diagram illustrating a plan view of one embodiment of a wafer on which multiple dies and multiple patterns of interest (POIs) are formed within the multiple dies.

In one embodiment, the POI has a width and a height that are shorter than a width and a height, respectively, of dies formed on the wafer and the other wafer. For example, FIG. 2 shows a wafer on which multiple dies are formed and multiple POIs are formed within each of the multiple dies. In particular, wafer 200 may be printed during a wafer fabrication process (e.g., lithography) with dies 202 in a certain layout. A first POI 204 may be located in a first position in the dies. For example, first POI 204 may be located in the upper left hand corner of the dies. In addition, as shown in FIG. 2, POI 204 has a width that is less than a width of the dies and a height that is less than a height of the dies. A second POI 206 is located in a second position in the dies different than the first position of the first POI. Furthermore, as shown in FIG. 2, POIs 204 and 206 may have different dimensions from each other. For instance, since POIs 204 and 206 include different DOIs detected in different patterns, the two POIs may have different dimensions that are determined based on the DOIs located in the different patterns. In addition, as shown in FIG. 2, POIs 206 have a width that is less than a width of the dies and a height that is less than a height of the dies. Furthermore, POIs can be partially overlapped.

In one embodiment, the pattern included in the target is preferably resolvable by an inspection system. The embodiments described herein will not work in non-pattern areas and will not work for randomly distributed defects.

In another embodiment, acquiring the information for the target includes grabbing templates for all known DOIs in one die, on the wafer or the other wafer, in which searching for target candidates as described further herein is performed with at least the first channel of the inspection system. The locations of these templates may be obtained by correlating the images of the targets with the images generated from the die for POI search. There may be many types of targets. One template may be grabbed for each type and for each channel. For example, as shown in FIG. 4, for an identified POI, template creation 410 may be performed to create POI template 412 for the identified POI. The template may be created in any manner described herein. Acquiring the information may also include defining the template location and size. In addition, acquiring the information may also include defining an area where one or more parameters may be determined for defect detection.

All templates may be grabbed from the same die for POI search. Due to relatively small variations in wafer structures, the image intensities of wafer patterns are sometimes substantially different across a wafer. This difference is referred to as color variation. Color variation is much smaller within a die than across a wafer. To ensure substantially high quality for POI search, all templates may be grabbed from one die and POI search may be performed on the die from which the templates are grabbed.

In one embodiment, acquiring the information for the target includes grabbing images of the known DOI with multiple channels of the inspection system, determining which of the grabbed images is best for detecting the known DOI in the target candidates described further herein, and designating one of the multiple channels with which the best of the grabbed images was grabbed as the second channel. For example, from among multiple images 402 shown in FIG. 4, the image that is best for defect detection may be determined. The channel(s) that were used to grab those image(s) may then be designated as the defect detection channel(s).

The images of the potential DOI and POI locations that are grabbed may be displayed to the user. The user can refine target candidates by reviewing images of POI and potential DOI locations and their similarity values. The POI locations are saved for defect detection. The target information and target candidate locations may be provided to defect detection.

The characteristics of POI and DOI may also be calculated. This target information will be saved for POI search which will be described later. For example, in one embodiment, the one or more characteristics include one or more characteristics of the known DOI. In one such example, defect information may be determined using test and reference images of sample defects. In particular, a reference image may be subtracted from a test image to generate a difference image, and the one or more characteristics of the known DOI may be determined from the difference image. In one such embodiment, the one or more characteristics include size, shape, intensity, contrast, or polarity of the known DOI. Defect size, shape, contrast, and polarity can be calculated using a difference image for the target. Intensity can be calculated from the test image of the target.

In the method shown in FIG. 4, from among multiple images 402, target information creation 406 may be performed. In an additional embodiment, the one or more characteristics include one or more characteristics of the known DOI determined from the second image acquired with the second channel, in this manner, target information creation may be performed using at least the image(s) that has or have been designated as the best for defect detection. For example, using the image(s) that has or have been determined to be the best for defect detection, one or more characteristics of the DOI such as those described herein may be determined, in this manner, the method may include determining defect information from the image types used for defect detection. Other target information 408 may also be created using multiple images 402 or the target information created in step 406. In this manner, different types of information may be determined for the target using any of the images that are grabbed for the wafer.

Different targets can share some of the same target information. For example, two DOIs may be located in or proximate to the same POI. The potential locations for these two DOIs can be defined relative to the POI location and can be identified by searching for the POI. In another example, two DOIs have the same characteristics, such as polarity. A defect polarity is defined by its gray level, which is either brighter or darker than its background.

The method may also include searching all POI locations from one die to determine if a DOI is in or near any of the POI locations. The potential DOI locations corresponding to these POI locations are referred to as target candidates. In this manner, the method may include searching for all target candidates (or potential DOI locations) in a die. The same pattern occurs at these locations, but DOI may or may not occur at these locations. Only if a DOI is detected at a location are the pattern and the defect an actual target. In some embodiments, the method includes searching an image of a die on the wafer or the other wafer for the POI by determining if a template for the target correlates with different portions of the image of the die. For instance, an inspection system may be used to grab images for an entire die and run a correlation (such as a normalized cross correlation (NCC)) between the template and images to search for the POI locations. The locations passing a correlation threshold value are target candidates. The user has an option to refine target candidates manually. The POI locations obtained from POI search are saved and will be used during defect detection.

As semiconductor design rules shrink, there is a higher chance for certain wafer structures to cause a defect. When those wafer structures are identified using design data such as graphical data stream (GDS) data, the structures are generally referred to as "hot spots," More specifically, "hot spots" may be identified by using GDS data to determine which wafer structures may (hypothetically) cause defects on the wafers. There may be different types of hot spots in one die, and the same type of hot spots may be printed at multiple locations in a die. Defects produced at hot spots are generally systematic defects and usually have weaker signals than surrounding noise making them relatively difficult to detect.

Hot spots are therefore different than the targets described herein in that the targets described herein are not identified as wafer structures in GDS data that may cause defects. Instead, the targets are identified using one or more actual wafers on which the wafer structures have been formed. For example, e-beam inspection or e-beam review may be used to find targets in substantially local areas. Because the throughput of e-beam inspection and e-beam review is generally substantially low, it typically cannot be used to inspect an entire wafer. However, the embodiments described herein can be used to, given a location of a target such as one found by e-beam inspection, determine how many target candidates are formed on the entire wafer and how many DOIs appear at these target candidates. In this manner, given a sample defect location, the method may determine how many of this kind of defect are on the wafer.

The embodiments described herein are, therefore, substantially different than methods that detect defects using GDS-based inspection. For example, GDS-based methods try to catch any type of defect and perform pixel-to-design alignment to generate images for run-time, swath-based alignment. In contrast, the methods described herein use an image of a sample DOI to find all defects of the same type on the entire wafer. The sample DOI can be from SEM review, e-beam inspection, or another inspection or defect review results file. During inspection, each POI location may be adjusted by correlating a template to the wafer image. Therefore, the two methods are not identical in that methods that use hot spots look for all possible defects while the methods described herein took for only specific known defects.

Setup of the methods described herein may also include any other suitable steps such as optics selection, which may be performed based on a known defect location. Some methods may also include inspecting any one target or one type of target with multiple optics modes of an inspection system. Optics modes are parameter configurations of wavelength, aperture, focus, light level, and the like for inspection systems. Such a method may include selecting one or more parameters for the multiple modes. In this manner, the method may include setting up more than one mode for the target-based inspection. Such a method may include using the best mode for defect signal to select DOI from different dies and collecting target information from one die. Collecting the target information may include grabbing defect images at the die locations obtained in the first step and performing inter-mode image alignment to find the corresponding template in another mode that is best for POI search. The method may then include finding all target candidate locations in one die using the search mode. The locations can then be viewed or revised based on image patches grabbed at these locations. The detection recipe may then be setup with the best mode for defect signal. Inspecting the target candidates may be further performed as described herein.

In comparison to using a single channel inspection system, which limits the inspection to using the same type of image for both pattern searching and defect detection, the embodiments described herein can use different types of images generated by different channels of an inspection system for 1) identifying the target location on the wafer and 2) performing defect detection at the target. Using different types of images for different functions during inspection provides a number of advantages to the embodiments described herein. For instance, some types of images may be good for wafer pattern sharpness while others may be good for defect signal. In one such example, a bright field (BF) mode may provide the best wafer image resolution, which is good for pattern searching. In addition, a dark field (DF) mode may provide the best defect signal and may be good for defect detection. In this case, two scans are required to obtain two types of images, and alignment between the two types of images is required. The embodiments described herein provide such capability by decoupling the pattern search sensitivity and defect detection sensitivity.

The method also includes searching for target candidates on the wafer or on another wafer. For example, as shown in FIG. 4, POI template 412 may be used for POI search 414.

The target candidates include locations of the POI on an entire die). There may be many locations with same type of pattern as a target. The same type of defect may occur at some of these locations. In order to detect all defects, these locations are searched and reported. To search these locations, the system may visit each pixel on the die and calculate a value for the similarity between the template and a pattern around the pixel on the die. If the similarity value is larger than a threshold defined at the template grab, the location of the pixel is marked as a POI location. The target candidate locations can be calculated by adding a position offset from POI to target candidate location.

In one embodiment, the first channel, at least in part, defines the best optics mode for image matching of the images of the target candidates to the first image or a template for the POI. In this manner, searching for the target candidates may be performed using the first image(s) acquired for the target using the best optics mode for image matching of the images of the target candidates to an image or a template for the POI. For example, the image of a POI, called a template, may be used to search entire logic areas to find all locations of potential defects by matching the templates to the wafer images, and the image that has the best pattern resolution may be used in POI location search. In this manner, POI searching may be performed with images obtained in an optics mode that is best for image matching. Acquiring target information and defect detection as described further herein may be performed using images obtained with different optics modes. For example, in one embodiment, imaging the target on the wafer is performed using a first optics mode, and the images of the target candidates used for detecting the known DOI in the target candidates are acquired using a second optics mode different than the first optics mode. Inter-mode image alignment may be performed between two optics modes.

In one embodiment, acquiring the information for the target and searching for the target candidates are performed using the inspection system (i.e., the same inspection system). In addition, acquiring the target information and searching for the target candidates may be performed with the inspection system in a setup step before defect detection. For example, the same inspection system should be used for template grab and POI search. Alternatively, acquiring the information for the target and searching for the target candidates are performed using different inspection systems of the same type. In this manner, acquiring the information for the target and searching for the target candidates may be performed using a different inspection system of the same type as the inspection system. In another embodiment, acquiring the information for the target and searching for the target candidates are performed in different dies on the wafer or the other wafer, and searching for the target candidates is performed in one die on the wafer or the other wafer using one or more templates for the target candidates.

In one embodiment, the target candidates can come from other sources, such as GDS-based pattern search. In these cases, the target-based inspection only needs to grab templates and compute the target information. Image-based search for POIs can be omitted.

In one embodiment, the method includes determining one or more parameters of a care area for the target-based inspection. In another embodiment, acquiring the information for the target includes specifying size, shape and location of care areas, size, shape and location of templates, and area where the one or more characteristics are determined in the images to which one or more detection parameters are applied (the images used for defect detection). For example, a micro care area (MCA) may be defined based on the locations of the target candidates identified in the searching step. In addition, the target locations can come from design files through rule-based or pattern-based search, and these locations can be used to create MCAs. A "care area" is a set of connected image pixels where defect detection is performed. Since the target candidate location is substantially accurate, an MCA can be defined around the location. An MCA size of a location around the target may be defined by a user with the help of a computer GUI. The size of the MCA can be, for example, 5 pixels by 5 pixels. In this manner, the method may include determining one or more parameters of a care area based on results of the searching step described herein. For example, as shown in FIG. 4, the method may include determining care areas 416 based on POI search 414. An MCA is created for each target candidate. In addition, as described further herein, MCAs may be generated to cover one or more of the potential DOI locations.

In this manner, during inspection, POI locations may be searched by correlating a template and the image generated for inspection. MCA locations may be corrected with the POI search result. During inspection, these locations are examined for any DOI activity. For example, defect detection may be performed by the computer system within the MCAs. MCAs serve as only approximate locations of defects, and the exact defect locations can be identified at run time based on the MCAs and the templates (image patches). The purpose of this step is to find approximate locations of potential defects, reduce the care areas for known DOIs and significantly exclude the areas that do not contain DOIs of known types and contain nuisance defects. Since the embodiments described herein use defect specific information, DOI detection and nuisance suppression are more effective.

Figure 2A:
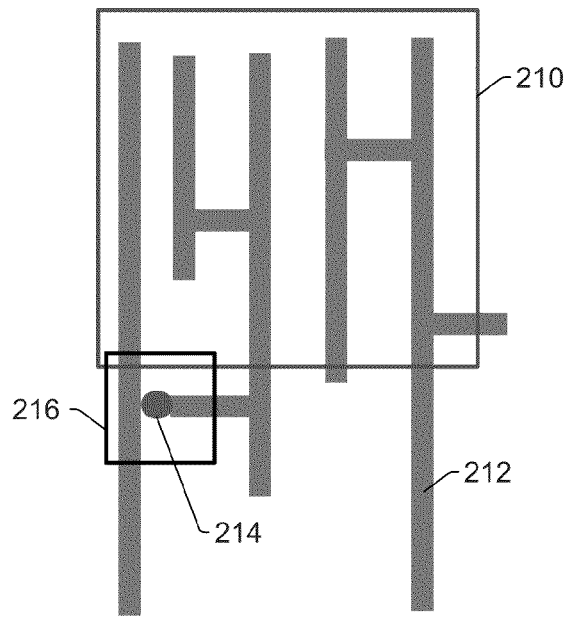
FIGS. 2a-2d are schematic diagrams illustrating plan views of different embodiments of a POI, one or more known DOIs occurring near or in the POI, and one or more micro care areas that may be generated for the known DOIs.
Figure 2B:
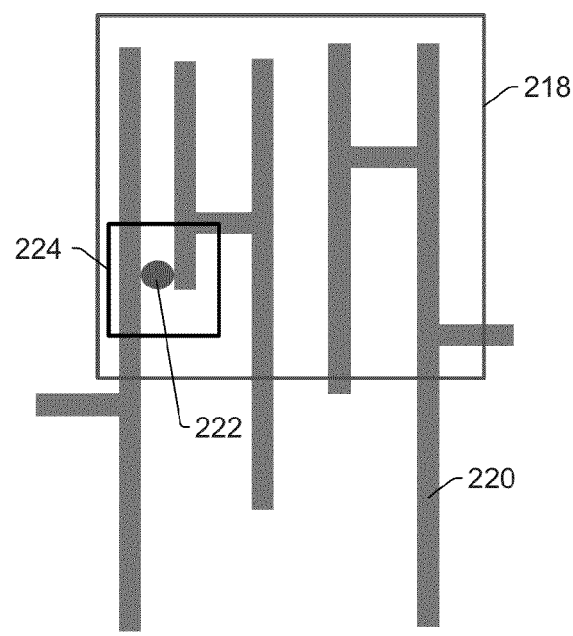
Figure 2C:
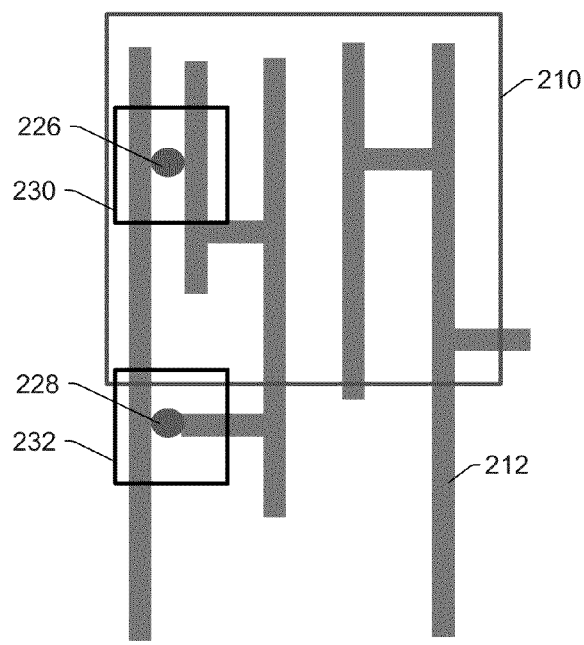
Figure 2D:
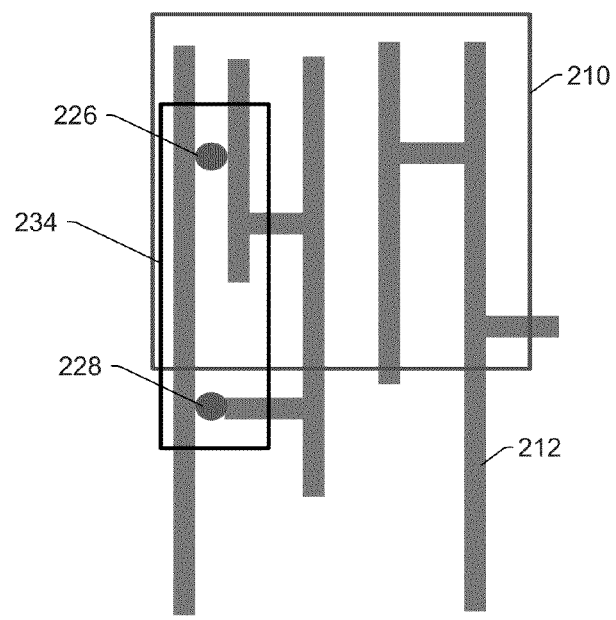

For each type of defect, one type of MCA around the locations that match the template may be generated. For example, for each type of defect, one type of MCA may be generated around the defect location based on a POI location. FIGS. 2a-2d show various relationships between a pattern on a wafer, a POI in the pattern, one or more DOIs located in and/or near the POI, and one or more MCAs that can be generated for each of the DOIs. For example, as shown in FIG. 2a, POI 210 may be located in pattern 212. The image of POI 210 shown in FIGS. 2a and 2c-2d is the POI as it may appear in a template for the POI. As shown in FIG. 2a, DOI 214 may be located near POI 210, but not necessarily in POI 210, MCA 216 may be positioned around and centered on the location of the DOI. In a similar manner, as shown in FIG. 2b, POI 218 may be located in pattern 220. The image of POI 218 shown in FIG. 2b is the POI as it may appear in a template for the POI. DOI 222 may be located in POI 218. MCA 224 may be determined around and centered on the location of the DOI. One POI can be associated with more than one DOI. For example, as shown in FIG. 2c, DOI 226 may be located in POI 210 while DOI 228 may be located near POI 210, but not necessarily POI 210. MCA 230 may be positioned around and centered on the location of DOI 226, while MCA 232 may be positioned around and centered on the location of DOI 228. Therefore, each of the MCAs may be associated with only one of the DOI. However, an MCA may be associated with more than one DOI. For example, as shown in FIG. 2d, MCA 234 may be generated for both DOI 226 and 228. POI and MCA shapes are not limited to a square or rectangle. The patterns shown in FIGS. 2a-2d are not intended to represent any pattern that may actually be formed on a wafer.

In one embodiment, the method includes determining a care area location by correlating a template image for the POI and the images used for the target candidates acquired by the first channel and applying the care area location to the images acquired by the second channel of the potential DOI locations. In this manner, the POI search may be performed using the images acquired with the best resolution or that have been determined to be best for pattern matching and the care area locations can be applied to the images determined to be best for defect detection. In addition, POI search and defect detection may be performed with two different wafer scans. The MCAs generated during POI search may serve as only approximate locations of defects during an inspection process. The exact defect locations can be identified by correlating the template with the image acquired with the best channel for pattern matching. Furthermore, the MCAs may not be accurately aligned with the potential defect locations. As such, during defect detection, a template may be correlated with the image acquired by the best channel for image matching to refine the MCA location. Such an embodiment may also include correcting wafer stage uncertainty. Then, defect detection can be performed within these MCAs as described further herein.

Figure 5:
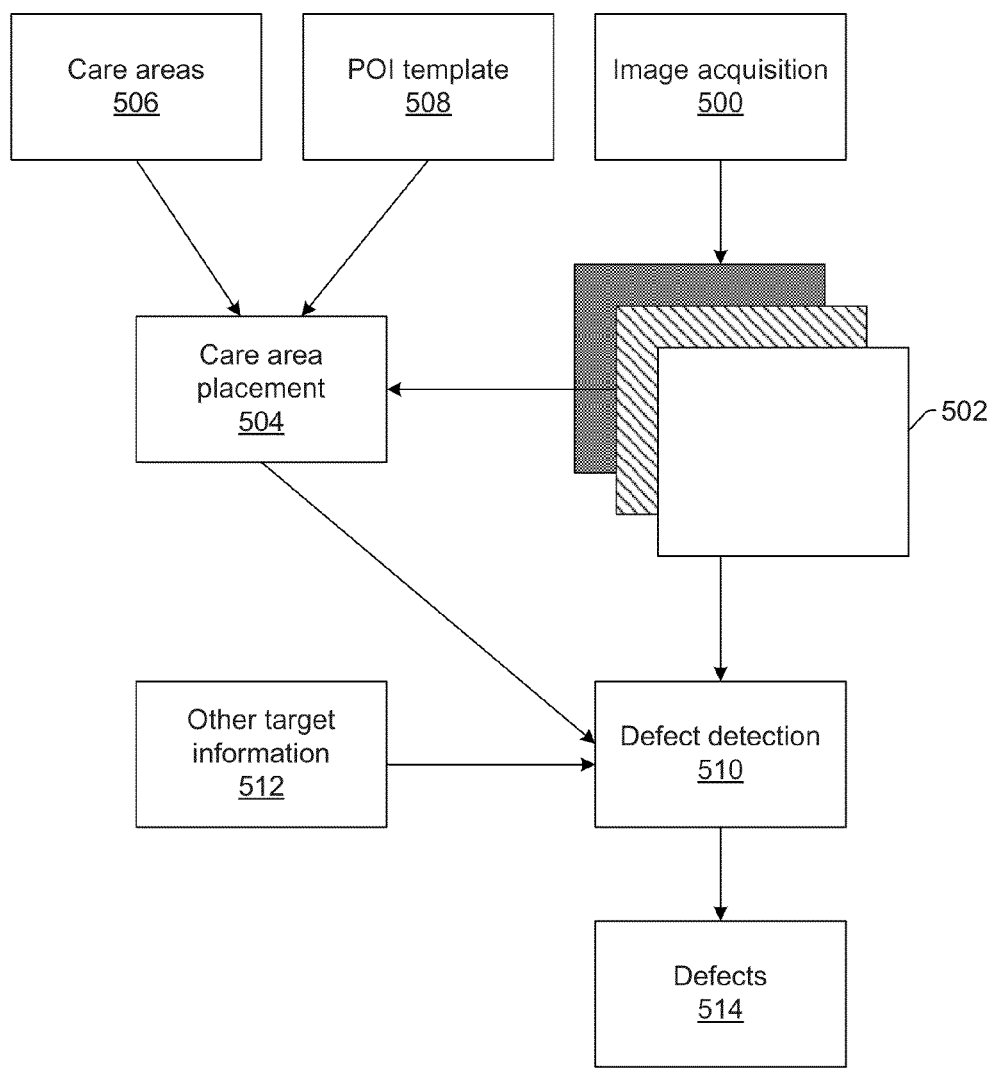
FIG. 5 is a flow chart strafing one embodiment of a method for multi-channel inspection.

In one such embodiment shown in FIG. 5, the method includes image acquisition 500, which may be performed as described herein using a multi-channel inspection system, which may be configured as described further herein. In this manner, image acquisition 500 may produce multiple images 502 generated by multiple channels of the inspection system. These images acquired from multiple channels are aligned to each other by the imaging system. As further shown in FIG. 5, care area placement 504 may be performed using at least one of multiple images 502, care areas 506, and POI template 508. For example, using information about the care areas, the POI template, and the image(s) that are best for pattern matching, the care area(s) may be placed in the image(s) that are best for defect detection. More specifically, once the POI template has been matched to one or more images that are best for pattern matching, information about where the POI template matches those one or more images as well as care area location relative to the POI location may be used to place a care area in another of the one or more multiple images that was or were generated using the channel(s) that is or are best for defect detection. As such, cross-channel information may be used to place care areas in images generated by fewer than all of the channels of an inspection system.

As further shown in FIG. 5, information about the care area placement as well as one or more of multiple images 502 may be used for defect detection 510. For example, once a care area has been placed in an image to be used for defect detection, one or more defect detection parameters may be applied to the image based on where the care area is located in the image. Such defect detection may be performed as described further herein. In addition, in some embodiments, other target information 512 may be used for defect detection 510. For example, as described further herein, information about the known DOI may be used for defect detection. As shown in FIG. 5, defects 514 may be detected by defect detection 510. The method shown in FIG. 5 may include any other step(s) described herein.

In this manner, target-based inspection may include only using image pixels in the care areas for the target candidates and as such, image pixels may not be used for non-target candidates on the wafer and inspection may not be performed for non-target candidates. Therefore, the embodiments described herein may be different than most inspection methods, which typically involve using image pixels in entire images. Such currently used methods are advantageous for a number of use cases such as detecting any defects that might be present in any locations on the wafer. However, these methods may not be able to find any DOI if the wafer noise is substantially high and DOI signal is relatively weak. Since the embodiments described herein are performed for only specific DOI that are present in only specific target candidates on a wafer, the embodiments are capable of detecting DOI that have relatively low signal-to-noise ratios with substantially high throughput while substantially suppressing nuisance defects in other areas. In addition, if there is only one location for a specific DOI, a POI search (setup step) can be bypassed.

In addition or alternatively to determining one or more parameters of a care area for the target, during setup the method may include identifying potential locations of target candidates on the wafer. For example, the positions of the targets within a die that will be formed on the wafer and information about the layout of the dies on the wafer may be used to identify potential locations of the target candidates on the wafer and therefore potential locations of the DOI on the wafer.

The method further includes detecting the known DOI in the target candidates by identifying potential DOI locations based on images of the target candidates acquired by the first channel and applying one or more detection parameters to the images acquired by the second channel of the potential DOI locations. In this manner, during inspection, multi-channel images are used for different purposes. In particular, the image type that is best for pattern search may be used to find substantially accurate locations of the MCAs. As such, the exact defect location can be found by applying pattern matching around the MCA using the template that is good for pattern matching. The defect information is used to determine whether a targeted defect exists at the specific locations. The image type best for defect detection is preferably used to detect defects. In particular, within the MCAs, the image that is best for defect detection is used to detect defects.

Detecting the DOI may include identifying the exact locations of the target candidates and checking whether the known DOI exists at the locations based on the defect information. More specifically, during inspection, MCAs, templates, and defect information generated during setup may be sent to a computer system such as that described further herein. For example, in one embodiment, the detecting step includes providing the information for the target to a defect detection module such as a computer system described herein in order to identify the potential DOI locations accurately. In this manner, the template may be used to find the exact location of the target candidates. For example, in one embodiment, the detecting step includes identifying the potential DOI locations in the images of the target candidates by correlating a template obtained during setup and the images of the target candidates obtained during defect detection.

The template may be correlated with the images acquired for the target candidates within a range using any suitable correlation such as NCC. This range is determined according to the wafer stage uncertainty and the inspection pixel size. A typical value is 20 pixels. The location of the pixel corresponding to the maximum NCC value is selected as the POI location. The target candidate location can be calculated based on the defect location relative to the POI location. In this manner, during inspection, the embodiments described herein find substantially accurate target candidate locations using image matching. The image types used for search during inspection are the same types used for search during set up.

In the case where multiple POI locations of the same target appear in one image, POI search is performed for one location and the offset from the approximate MCA location to the true MCA location is calculated. This offset is applied to other approximate MCA locations in this image. It is not necessary to search for all POI locations.

Since the embodiments described herein perform target-based alignment to substantially accurately locate all potential defect locations, the embodiments described herein are advantageous over swath alignment-based approaches which may be used in design-based methods. A swath is the raw image generated by a time delay integration (TDI) sensor that covers an entire die row. Swath-based alignment correlates the care areas to the swath image. Swath-based alignment may fail for a relatively small percentage of the inspection data. If such misalignment happens, the whole swath will not be inspected or a substantial amount of nuisance defects will be detected and reported due to misaligned inspection data. However, the embodiments described herein will be immune to such alignment issues because the target-based correlations described herein are performed locally.

Applying one or more detection parameters to the images for the target candidates may be performed in any suitable manner. For example, in some embodiments, applying the detection parameter(s) includes generating difference images using the images of the potential DOI locations and a reference image, calculating a noise measure and a threshold, and applying a threshold to signals in the difference images. In another embodiment, the method includes determining one or more characteristics of difference images proximate to the potential DOI locations, and applying the detection parameter(s) includes applying a threshold to one or more values of the one or more characteristics of the difference images. The reference image may be, for example, an image of the potential DOI location in a die in which the DOI has not been detected, a median image of multiple dies, or a template acquired at setup. For example, in one embodiment, the images of the potential DOI locations to which the detection parameter(s) are applied include images generated using a reference image and a test image, and the reference image is a template for the POI. In this manner, the reference image may not be an image acquired during inspection. In other words, the reference image is not limited to an image acquired during inspection. In another example, a location of a non-defective target candidate may be identified on the wafer and an image may be acquired at the location on the wafer using the inspection system. This image may be subtracted from the image acquired at the location of another target candidate to generate a difference image, and a threshold such as that described herein may be applied to the difference image. Any signals in the difference image above the threshold may be identified as a defect or a potential defect. Detecting the known DOT is performed using a computer system, which may be configured as described further herein.

The method of using a template as the reference image is advantageous in certain situations. For example, if the number of systematic defects is substantially high, a majority of the dies on a wafer will be defective. If two defects appear at the same die location on two neighboring dies, the difference image between images of these two dies may not reveal the defect. It is substantially likely that a median of multi-die images is defective. Thus, the median image cannot be used as the reference image. The reference image may be determined at setup and verified as defect free. Therefore, it can be used during inspection.

In some embodiments, the method includes determining the detection parameter(s) based on the information for the target. For example, the detection parameter(s) (or the defect detection algorithm) may be noise adaptive. That is, if noise is relatively high in the images acquired for the target, the inspection sensitivity may be set relatively low. Otherwise, the inspection sensitivity may be set relatively high. The inspection sensitivity may be set relatively low by selecting a relatively high threshold that is applied to difference images for the target candidates. In contrast, the inspection sensitivity may be set relatively high by selecting a relatively low threshold that is applied to difference images for the target candidates. In addition, in another embodiment, the method includes determining the detection parameter(s) separately for each target type based on images for each target type, respectively. Therefore, since the methods can be used for different types of targets, different thresholds can be used for detecting defects in different types of target candidates. For instance, a first threshold may be used for detecting a first known DOI in a first type of target candidate, and a second, different threshold may be used for detecting a second, different known DOI in a second, different type of target candidate.

The same detection parameter(s) may be used to detect defects in each of the target candidates having the same target type. However, in another embodiment, the method includes determining the detection parameter(s) separately for each of the target candidates for which detecting the known DOI is performed based on the images of the target candidates, respectively. In this manner, the detection parameter(s) may be determined on a target candidate-by-target candidate basis. For example, once a potential target candidate or potential DOI location has been identified, the standard deviation of the difference image in a local area may be determined. The threshold may then be determined as threshold=Mean+G+K*StandardDeviationOf (difference in a local area), where Mean is the average value of the difference image in a local area and G and K are user-defined parameters. G and K are signed values. However, the threshold for each target candidate may be determined in any other suitable manner.

The DOI information may also be used to determine whether a known DOI exists at the potential DOI locations. For example, in an additional embodiment, the one or more characteristics include characteristic(s) of the known DOI such as any of those described above, and applying the detection parameter(s) includes applying a threshold to one or more values of the characteristic(s) determined from the images of the potential DOI locations. In one such example, if a characteristic of the known DOI such as polarity is consistent from DOI to DOI, then detecting the DOI may include thresholding the values for the characteristic. Such polarity-based thresholding can be applied to the image acquired for the target candidate that correlates to the template or a difference image generated as described above for the target candidate. Thresholding of the defect characteristic(s) may be used in combination with other thresholding described herein (e.g., thresholding the signals in the difference images). Using defect characteristics such as polarity and defect size in this manner can also be helpful for suppressing nuisance defects.

Figure 3:
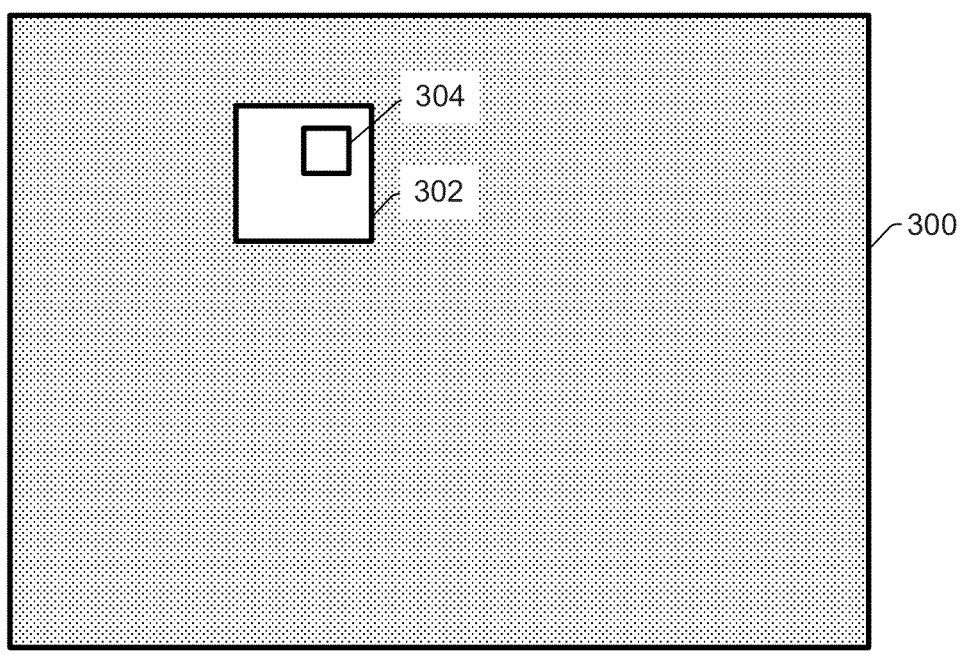
FIG. 3 is a schematic diagram illustrating a plan view of one embodiment of an image, an area within the image that is used to determine one or more detection parameters, and an area within the image to which the one or more detection parameters are applied.

In a further embodiment, the images of the potential DOI locations to which the detection parameter(s) are applied are images of care areas surrounding the potential DOI locations, and the care areas are determined based on a size of the known DOI occurring proximate to or in the POI. For example, the size of the image that is acquired at roughly the location of the target candidate may be relatively large to be sure that an image is actually acquired for the target candidate. In one such example, area 300 shown in FIG. 3 may be roughly the size of the image that was acquired at the target candidate. In addition, area 300 may be the size of the difference image generated for the target candidate. The location of the target candidate within that image may then be determined using correlation as described above. An area known to be larger than the target candidate may then be used to determine a threshold on a target candidate-by-target candidate basis as described above. For example, as shown in FIG. 3, area 302 within area 300 may be used to determine the threshold for the target candidate. The threshold may then be applied to an area slightly larger than the area of the known DOI. For example, as shown in FIG. 3, area 304 within area 302 may be the area to which the threshold is applied, and area 304 may be slightly larger than the area of the known DOI. In one such example, the portion of the image used to determine the threshold may be about 64 pixels by about 64 pixels while the area to which the determined threshold is applied may be about 5 pixels by about 5 pixels, depending on the size of the known DOI. Reducing the size of the difference image to which the threshold is applied reduces the possibility that noise in the image will be mistakenly identified as a potential DOI. In addition, using such a substantially small area as the care area to which the threshold is applied allows the use of a substantially low threshold without detecting overwhelming nuisance defects. For this reason, the care area used in this embodiment is referred to as a micro care area or MCA. In contrast, many currently used inspection methods that use relatively low thresholds for substantially sensitive inspection detect huge amounts of nuisance defects that have to then be separated from the DOIs.

In one embodiment, the method includes selecting one or more characteristics of the target, selecting the detection parameter(s), and determining one or more parameters of a care area such that nuisance defects other than the known DOI are not detected in the target candidates (e.g., only locations in which the known DOI likely occur are inspected). For example, the care areas may be reduced to include areas only for known DOIs and to substantially exclude the areas that do not contain known DOIs and only contain nuisance defects. In particular, the care areas can be defined around the locations where known DOI may occur. Therefore, noise outside of the care areas can be completely ignored. In addition, since the image of the target or a template can be used to find substantially exact locations of the target candidates, the care areas can be made substantially small. The care areas used in the embodiments described herein may also be substantially smaller than other currently used care areas since other methods do not have a mechanism to locate target candidates substantially accurately. The more accurate the target candidate locations can be determined, the smaller the care area that can be used and the less nuisance defects will be detected. In addition, the embodiments described herein can detect systematic defects by refining care area locations that originate from design data.

Although the embodiments are described herein with respect to searching for target candidates and detecting the known DOI in the target candidates, it is to be understood that the embodiments described herein can be used to search more than one type of target candidate and to detect DOI in more than one type of target candidate. For example, there may be multiple types of bridge defects on a wafer, or the same type of bridge may occur in different wafer structures. These bridges can be treated as different types of targets. The embodiments described herein may include using the information about these types of targets to search an entire die for any other instances of the target candidates. MCAs are defined around these target candidates and their locations are refined during inspection. Defect detection may be performed for each instance of the target candidates. In this manner, the embodiments described herein may be used to inspect target candidates across an entire wafer.

In one embodiment, none of the steps of the method are performed using design data for the wafer or the other wafer. In other words, design data for the wafer or the other wafer is not required for any step of the method. Therefore, the embodiments described herein are advantageous in that they do not require design data. Instead, inspection images other than GDS information are used. As such, GDS availability is not an issue. In contrast, methods that use hot spots require design data in order to be performed. Such methods sometimes also need support from someone (e.g., a customer) with design knowledge. However, since the embodiments described herein do not require any design data, any user can perform the inspection, which is a significant advantage particularly since the design data may not be available in all instances.

In one embodiment, each step of the method independently may use design data for the wafer or the other wafer. For example, the embodiments described herein can work with information provided from design data. For example, a design engineer may indicate a wafer structure that is prone to a bridge defect and would like to monitor the location. Target information can be generated, and a search can be performed in a die to find all target candidates having the same pattern as the target. Defect detection can be performed in these target candidates to find other targets on this wafer or other wafers. In another embodiment, design-based pattern search can be performed to find all target candidates on a die. The embodiments described herein can generate target information, skip the image-based search and perform defect detection at these target candidates.

The embodiments described herein may also be performed as design-based inspection. For example, all target candidate locations can be used as hot spot locations. Design-based inspection creates relatively small care areas around hot spots and performs pixel-to-design alignment to refine care area locations. Then, defect detection is performed at hot spots.

Signals in the images of the target candidates corresponding to the known DOI may be approximately equal to or weaker than signals corresponding to nuisance defects on the wafer. For example, a regular inspection may involve performing defect detection in inspection care areas that cover most of the area of the die. In situations in which signals for DOIs are much weaker than false (nuisance) defects, overwhelming false defects can be detected by existing approaches. For example, in order to detect defects with relatively weak signals, a substantially sensitive inspection may be performed, which also detects many nuisance defects. The nuisance count may be more than 99% of the total detected events. It is substantially difficult to find DOI among such massive amounts of nuisance defects. For example, feature vectors and defect attributes may be computed for each defect from images and used in defect classification. However, sometimes, the DOIs cannot be separated from nuisance defects because these two types of events can occupy the same areas in feature vector and attribute space. Therefore, extra information must be used to solve this problem. Furthermore, if a less sensitive inspection is used, the nuisance rate can be significantly reduced but DOI may also be lost i.e., undetected).

In contrast, the embodiments described herein suppress huge amounts of nuisance defects. For example, the embodiments described herein use information that targets on specific DOI and is very relevant for defect detection. Classification approaches remove nuisance defects after nuisance events are detected. The embodiments described herein attempt to prevent nuisance events from being detected. More specifically, the embodiments described herein allow a highly sensitive inspection to be run while controlling the nuisance defect count by inspecting the wafer in areas (i.e., the target candidates) in which the known DOI will likely appear. In other words, using substantially accurate defect location information as described herein is a major contributor to nuisance suppression. In this manner, the embodiments described herein can achieve significant nuisance defect suppression for known DOIs with relatively weak signals in repeating structures. Thus, the embodiments described herein can detect DOIs and suppress nuisance defects more accurately.

The embodiments described herein may be complementary to any other inspection that may also be used to inspect the wafer. For example, in another embodiment, the method includes acquiring other images for the wafer or the other wafer and using the other images to detect other defects on the wafer or the other wafer. In one such example, for other areas (e.g., areas other than the care areas), a regular inspection may be setup and run as usual to detect randomly-distributed defects and the embodiments described herein may be run to detect systematic defects with relatively weak signals. In addition, detecting the known DOIs as described herein and regular inspection can be performed in one test thereby providing significant throughput advantages. For example, the embodiments described herein may be used to detect known DOIs with relatively weak signals and can be run in parallel with any general inspection approach.

The embodiments described herein may also be used for specific nuisance defect removal. For example, the embodiments described herein may be performed as described herein but instead of being performed for a known DOI, the embodiments can be performed for a known systematic nuisance defect. The known nuisance defects can be defined as removal targets. A don't care area can be defined for removal targets. The embodiments described herein can search removal target candidates on a die, define a don't care area around the removal candidate and not perform defect detection in the don't care area. Thus, this type of nuisance defect will not be detected.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method detects the defects, the method may include storing information about the detected defects in a storage medium.

Figure 6:
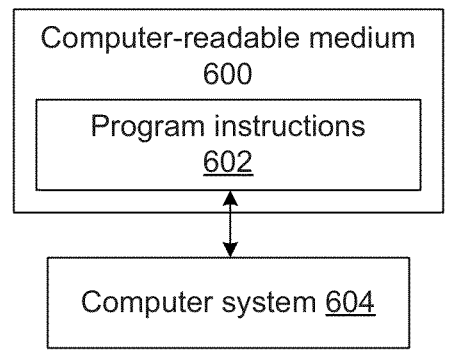
FIG. 6 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for detecting defects on a wafer. One such embodiment is shown in FIG. 6. In particular, as shown in FIG. 6, non-transitory computer-readable medium 600 includes program instructions 602 executable on computer system 404. The computer-implemented method includes the steps of the method described above. The computer-implemented method for which the program instructions are executable may include any other step(s) described herein.

Program instructions 602 implementing methods such as those described herein may be stored on computer-readable medium 600. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MCF"), or other technologies or methodologies, as desired. The program instructions can be run on any processors, such as CPU, GPU etc.

The computer system may take various forms, including a personal computer system, image computer, mainframe computer system, workstation, network appliance, Internet appliance, or other device. A computer system can have a single core or multi-cores. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 7:
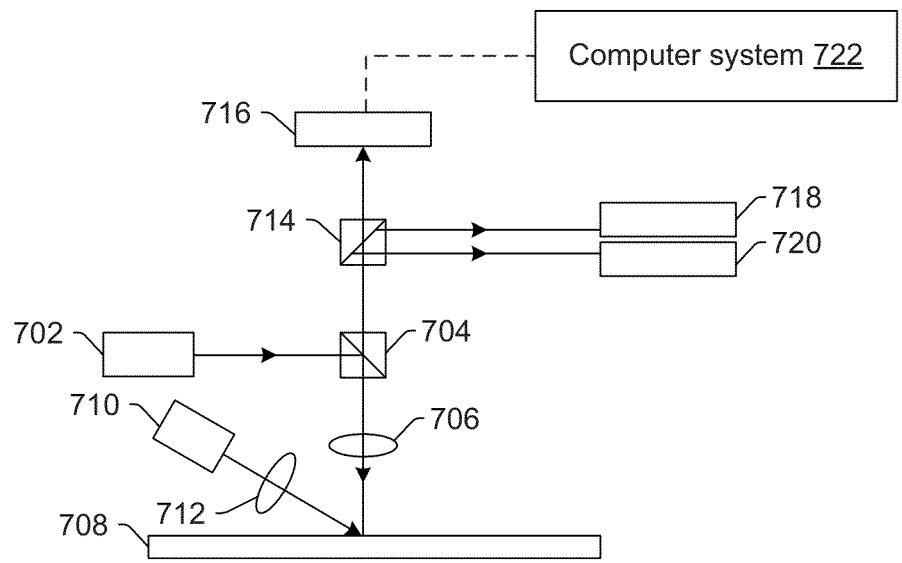
FIG. 7 is a schematic diagram illustrating a side view of one embodiment of a system configured to detect defects on a wafer.

Another embodiment relates to a system configured to detect defects on a wafer. One embodiment of such a system is shown in FIG. 7. The system includes an inspection subsystem configured to acquire information for a target on a wafer. The inspection subsystem may include any suitable inspection subsystem such as an e-beam inspection (EBI) or electron beam review (EBR) subsystem. Examples of suitable EBI subsystems include those that are included in commercially available FBI tools such as the eSxxx tools from KLA-Tencor, Milpitas, Calif., and tools from other suppliers such as Hermes Microvision, Inc., Hsinchu City, Taiwan, or NGR Inc., Yokohama, Japan, Electron beam subsystems can collect images in multiple modes, and the images can be used either in a die-to-die comparison, a cell-to-cell comparison, or a die-to-database comparison. Alternatively, the inspection subsystem may include an optical inspection subsystem, which may have a configuration as described herein.

The target includes a POI formed on the wafer and a known DOI occurring proximate to or in the POI. The target may be further configured as described herein. The information includes a first image of the POI on the wafer acquired by imaging the POI on the wafer with a first channel of the inspection subsystem and a second image of the known DOI on the wafer acquired by imaging the known DOI with a second channel of the inspection subsystem. The image of the target may include any suitable data, image data, signals or image signals. The inspection subsystem may image the target on the wafer in any suitable manner. The information for the target may include any other target information described herein.

The inspection subsystem is also configured to search for target candidates on the wafer or another wafer. The target candidates include the POI. The target candidates may be configured as described herein. As shown in FIG. 7, the inspection subsystem includes light source 702. Light source 702 may include any suitable light source known in the art such as a laser. Light source 702 is configured to direct light to beam splitter 704, which is configured to reflect the light from light source 702 to refractive optical element 706. Refractive optical element 706 is configured to focus light from beam splitter 704 to wafer 708. Beam splitter 704 may include any suitable beam splitter such as a 50/50 beam splitter. Refractive optical element 706 may include any suitable refractive optical element, and although refractive optical element 706 is shown in FIG. 7 as a single refractive optical element, it may be replaced with one or more refractive optical elements and/or one or more reflective optical elements.

Light source 702, beam splitter 704, and refractive optical element 706 may, therefore, form an illumination channel (referred to herein as the "first illumination channel") for the inspection subsystem. The illumination channel may include any other suitable elements (not shown in FIG. 7) such as one or more polarizing components and one or more filters such as spectral filters.

As shown in FIG. 7, the light source, beam splitter, and refractive optical element are configured such that the light is directed to the wafer at a normal or substantially normal angle of incidence. However, the light may be directed to the wafer at any other suitable angle of incidence. For example, the inspection subsystem may include a second illumination channel that is configured to direct light to the wafer at an oblique angle of incidence. In the embodiment shown in FIG. 7, for example, the inspection subsystem may also include light source 710 that is configured generate light and may include any suitable light source. The inspection subsystem may also include refractive optical element 712 that is configured to focus light from light source 710 to wafer 708 at an oblique angle of incidence. Therefore, light source 710 and refractive optical element 712 form another illumination channel for the inspection subsystem. This second illumination channel may also include any other suitable elements (not shown in FIG. 7) such as those described above.

In the embodiment shown in FIG. 7, therefore, the inspection subsystem may include two different light sources that are included in two different illumination channels. The two different light sources may have the same configuration or different configurations. For example, the light sources may be different lasers having different configurations. In addition, the light sources may generate light having the same characteristics or one or more different characteristics. In one such example, the light generated by the different light sources may have different wavelengths and/or different polarizations. Furthermore, the inspection subsystem may include only one light source in place of the two shown in FIG. 7 and the light from the light source may be split into two different beams that are used by two different channels for illumination of the wafer.

The inspection subsystem may be configured to scan the light over the wafer any suitable manner.

Light reflected from wafer 708 due to illumination by the first illumination channel described above may be collected by refractive optical element 706 and may be directed through beam splitter 704, and possibly beam splitter 714, to detector 716. Therefore, the refractive optical element, beam splitters, and detector may form a detection channel (also referred to herein as the "first detection channel") of the inspection subsystem. The detector may include any suitable imaging detector known in the art such as a charge coupled device (CCD). This detection channel may also include one or more additional components (not shown in FIG. 7) such as one or more polarizing components, one or more spatial filters, one or more spectral filters, and the like. Detector 716 is configured to generate an image that is responsive to the reflected light detected by the detector.

As shown in FIG. 7, the first illumination channel is configured to direct light to the wafer through the same refractive optical element used for collecting light from the wafer. Therefore, the first illumination channel, as shown in FIG. 7, is configured as a "through-the-lens" illumination channel. In addition, since the second illumination channel does not direct light to the wafer through the refractive optical element that is used for collecting light from the wafer, the second illumination channel is configured as an "outside-the-lens" illumination channel. The inspection subsystem may include any suitable one or more "through-the-lens" illumination channels and/or one or more "outside-the-lens" illumination channels.

Light reflected from wafer 708 due to illumination by the first illumination channel described above that is collected by refractive optical element 706 may also be directed through beam splitter 704 to beam splitter 714 that reflects at least a portion of the collected light to detectors 718 and 720. Therefore, the refractive optical element, beam splitters, and detector 718 may form a detection channel (also referred to herein as the "second detection channel") of the inspection subsystem, and the refractive optical element, beam splitters, and detector 720 may form a detection channel (also referred to herein as the "third detection channel") of the inspection subsystem. The detectors and their respective detection channels may be further configured as described above. In some instances, the inspection subsystem may be configured such that light from beam splitter 714 is directed to only one detector (not shown in FIG. 7), which may be configured as described above.

As described above, each of the detectors included in the inspection subsystem may be configured to detect light reflected from the wafer. Therefore, each of the detection channels included in the inspection subsystem may be configured as Bright-Field channels. However, one or more of the detection channels may be used to detect light scattered from the wafer due to illumination by one or more of the illumination channels. For instance, in the embodiment shown in FIG. 7, detector 716 may be used to detect light reflected from the wafer due to illumination by the first illumination channel, and detectors 718 and 720 may be used to detect light scattered from the wafer due to illumination by the second illumination channel. In another example, detectors 716, 718, 720 may each be used to detect light reflected from the wafer due to illumination by the first illumination channel, the illumination channel used for illumination of the wafer may be switched, and each of the detectors may then be used to detect light scattered from the wafer due to illumination by the second channel. The illumination channel used for illumination of the wafer may be switched in any suitable manner (e.g., by manipulation of one or more shutters (not shown in FIG. 7), which may be included in one or more of the illumination channels). Images acquired through any channel can be used for POI search or defect detection.

Furthermore, although the inspection subsystem is shown in FIG. 7 as including one collection lens (i.e., refractive optical element 706) that collects the light that is detected by all of the detectors (and therefore all of the channels) of the inspection subsystem, the inspection subsystem may include more than one collection lens, and one or more detectors may be used to detect the light collected by each collection lens. In this manner, collections optics may be separate for the various channels.

The system also includes computer system 722 configured to detect the known DOI in the target candidates by identifying potential DOI locations based on images of the target candidates acquired by the first channel and applying one or more detection parameters to images acquired by the second channel of the potential DOI locations. The computer system may identify the locations and apply the one or more detection parameters as described further herein. In addition, the computer system may be configured to perform any other step(s) described herein.

Images generated by all of the detectors included in each of the detection channels of the inspection subsystem may be provided to computer system 722. For example, the computer system may be coupled to the detectors (e.g., by one or more transmission media shown by the dashed lines in FIG. 7, which may include any suitable transmission media known in the art) such that the computer system may receive the images generated by the detectors. The computer system may be coupled to the detectors in any suitable manner. The computer system may be further configured as described herein. The inspection subsystem may also be further configured as described herein. Furthermore, the system may be further configured as described herein.

As noted above, a key part of the embodiments is acquiring multiple images of the same location on a wafer through more than one channel, simultaneously or sequentially, from different perspectives, with different spectra (i.e., wavelength bands), apertures, polarizations, imaging mechanisms, or some combination thereof. Some images may be better for pattern resolution while some are better for defect detection.

Multiple images may be collected simultaneously through separate multiple channels in the same inspection system such as that described above or using two channels (e.g., Channel 1 and Channel 2) of a Dark-Field system like Puma 9650 that is commercially available from KLA-Tencor. Alternatively, multiple images may be collected sequentially (i.e., multi-pass) on either a multi-channel system (e.g., Channel 1 and Channel 2 of Puma performed in a multi-pass scenario with two different polarizations) or a single-channel system (e.g., Vanquish with two different apertures or a single channel on a multi-channel system such as Puma). The two or more channels used in the embodiments described herein may also include two or more collection channels configured for different ranges of numerical aperture (e.g., as in the Puma system). Obviously, many combinations of channels with many combinations of configurations can be used in the embodiments described herein.

Various inspection architectures offered by KLA-Tencor and other companies can be used to implement the embodiments described herein including the line-illumination architecture on KLA-Tencor's Puma, the spot-illumination architecture on UV-Vision, which is commercially available from Applied Materials, Inc., Santa Clara, Calif., and the flood-illumination architectures on patterned inspection systems from Hitachi High Technologies America, Inc., Pleasanton, Calif., and Negevtech Ltd., Santa Clara, Calif. Some of these systems, e.g., those from Hitachi and Negevtech, originally use a single channel and can be adapted to add one or more additional channels, which would allow them to collect multiple images in one pass or multiple passes. Some of these systems, e.g., Applied Materials' UV-Vision, already have multiple channels, e.g., BF and DF channels, so they could collect multiple images in one pass or multiple passes. Applied. Materials' DF systems such as ComPlus, Sting, and DFinder all have multiple channels as well. All of these wafer inspection systems and architectures, from KLA-Tencor and other companies, can be used with the multi-image embodiments described herein.

In some embodiments such as that shown in FIG. 7, the system may use through-the-lens illumination and that illumination can be single spot, multi-spot, flood, or line illumination, in addition, any such illumination configurations may be used with separate and simultaneous BF and DF (or grayfield (GF)) collection. For example, as described above with respect to FIG. 7, the light from the wafer due to illumination by the first illumination channel can be collected and detected by multiple channels, each of which may be configured to detect reflected light (as in a BF configuration) or scattered light (as in a DF configuration). In some such configurations, the illumination may be directed through only a portion of the lens (i.e., refractive optical element 706) or collection optics, while different portions of the NA of that lens or collection optics may be used for only DF or BF detection. In other words, the inspection subsystem may be configured such that light in a first portion of the collection NA is directed to only some detectors of the inspection subsystem while light in a second portion of the collection NA is directed to only some other detectors of the inspection subsystem. Therefore, different portions of the collection NA may be detected mutually exclusively by different detection channels of the inspection subsystem.

Figure 8:
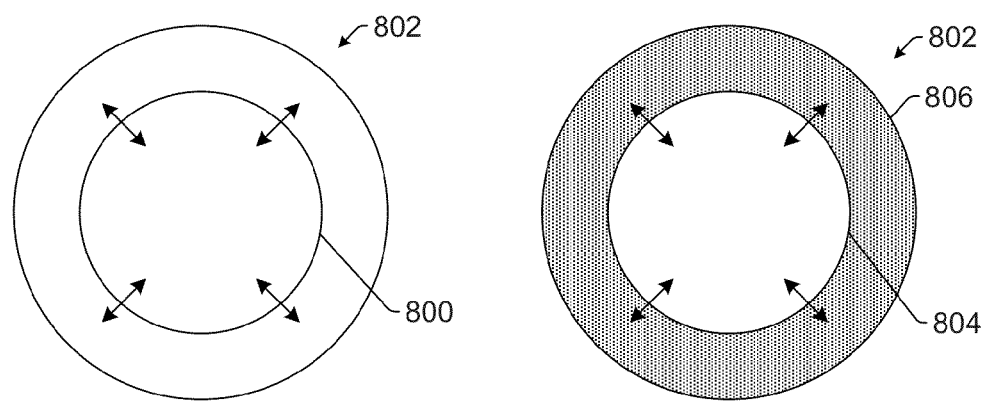
FIGS. 8 and 9 are schematic diagrams illustrating plan views of various embodiments of illumination and collection schemes that can be used by the embodiments described herein.

In one such embodiment shown in FIG. 8, through-the-lens illumination may be performed by directing light through portion 800 of collection NA 802. For example, in the embodiment shown in FIG. 8, beam splitter 704 shown in FIG. 7 may be configured to direct light from light source 702 through only portion 800 of the collection NA. In one such embodiment, as shown in FIG. 8, the light from the wafer in portion 804 of the collection NA may be directed to only one or more BF channels while light in portion 806 of the collection NA may be directed to only one or more DF channels. For example, in one such embodiment, substantially all of the light in portion 804 of the collection NA may be allowed to pass through beam splitters 704 and 714 of the system shown in FIG. 7 to one or more BF channels (e.g., the detection channel that includes detector 716) while substantially all of the light in portion 806 shown in FIG. 8 may be transmitted by beam splitter 704 and reflected by beam splitter 714 to one or more DF channels (e.g., one or more of the detection channels that include detectors 718 and 720 shown in FIG. 7). In one such embodiment, beam splitter 714 may be configured to have a substantially transmissive central portion that corresponds to portion 804 of the collection NA and a substantially reflective outer, annular portion that corresponds to portion 806 of the collection NA. Therefore, the light detected by the BF channel(s) is mutually exclusive of the light detected by the DF channel(s) and vice versa. (The double-headed arrows shown in FIG. 8 indicate that the boundaries of the illumination and collection NAs are arbitrary.)

In some embodiments such as that shown in FIG. 7, the system may use outside-the-lens illumination and that illumination can be single spot, multi-spot, flood, or line illumination. In addition, any such illumination configurations may be used with multiple DF collection channels. In this manner, any such illumination configurations may be used with separate and simultaneous multi-DF collection. For example, as described above with respect to FIG. 7, the light from the wafer due to illumination by the second illumination channel can be collected and detected by multiple channels, each of which may be configured to detect scattered light (as in a DF configuration). In some such configurations, different portions of the NA of the lens (i.e., refractive optical element 706) may be used for only corresponding, different DF detection. In other words, the inspection subsystem may be configured such that scattered light in a first portion of the collection NA is directed to only some detector(s) of the inspection subsystem, scattered light in a second portion of the collection NA is directed to only some other detector(s) of the inspection subsystem, etc. Therefore, different portions of the collection NA may be detected and used mutually exclusively by different DF detection channels of the inspection subsystem.

Figure 9:
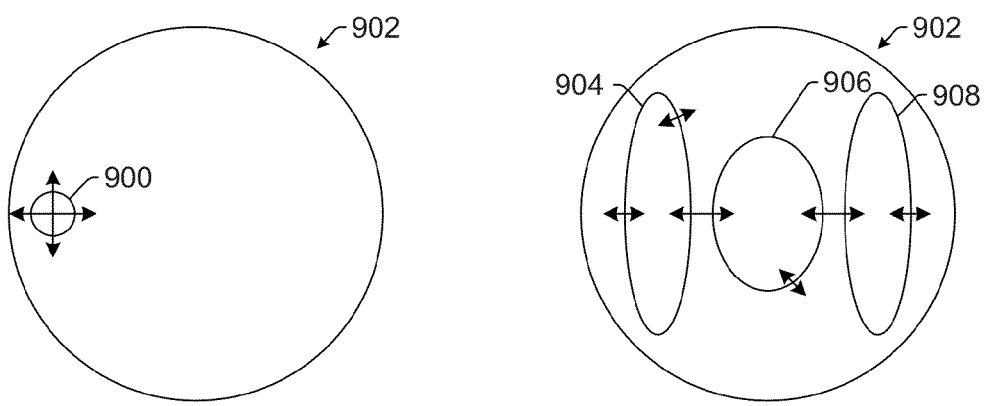

In one such embodiment shown in FIG. 9, outside-the-lens illumination may be performed by directing light to an area on the wafer corresponding to portion 900 of collection space 902 of the inspection subsystem. For example, in the embodiment shown in FIG. 9, refractive optical element 712 of the system shown in FIG. 7 may be configured to direct light from light source 710 to an area on wafer 708 corresponding to portion 900 of the collection space. In one such embodiment, the scattered light from the wafer in portion 904 of the collection space may be directed to only a first DF channel, while scattered light in portion 906 of the collection space may be directed to only a second DF channel and scattered light in portion 908 of collection space 902 may be directed to only a third DF channel. For example, with reference to the embodiment shown in FIG. 7, substantially all of the light in portion 904 of the collection space may be reflected by beam splitter 714 to detector 718, substantially all of the light in portion 906 of the collection space may be transmitted by beam splitter 714 to detector 716, and substantially all of the light in portion 908 of the collection space may be reflected by beam splitter 714 to detector 720. In this configuration, each of the detectors shown in FIG. 7 may be used for scattered light detection. In this manner, each of the detection channels shown in FIG. 7 may be used as DF channels. In one such embodiment, beam splitter 714 may be configured to have a substantially transmissive central portion that corresponds to portion 906 of the collection space and substantially reflective outer portions that correspond to portions 904 and 908 of the collection space. Therefore, the light detected by each of the DF channel(s) is mutually exclusive of the light detected by each other DF channel(s) and vice versa. (The double-headed arrows shown in FIG. 9 indicate that the boundaries of the illumination and collection NAs are arbitrary.)

It is noted that FIG. 7 is provided herein to generally illustrate one configuration of an inspection subsystem that may be included in the system embodiments described herein. Obviously, the inspection subsystem configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 28XX, 29XX, and Puma 9XXX series of tools that are commercially available from KLA-Tencor and any of the other commercially available tools noted above. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
   acquiring information for a target on a wafer, wherein the target comprises a pattern of interest formed on the wafer and a known defect of interest occurring proximate to or in the pattern of interest, and wherein the information comprises a first image of the pattern of interest on the wafer acquired by imaging the pattern of interest on the wafer with a first channel of an inspection system, a second image of the known defect of interest on the wafer acquired by imaging the known defect of interest with a second channel of the inspection system, a location of the pattern of interest on the wafer, a location of the known defect of interest relative to the pattern of interest, and one or more characteristics computed from the pattern of interest and the known defect of interest;
   searching for target candidates within one die on the wafer, or on another wafer, wherein the target candidates comprise the pattern of interest; and
   detecting the known defect of interest in the target candidates by identifying potential defect of interest locations based on images of the target candidates acquired by the first channel and applying one or more detection parameters to images acquired by the second channel of the potential defect of interest locations, wherein said detecting is performed using a computer system.

2. The method of claim 1, wherein design data for the wafer or the other wafer is not required for any step of the method.

3. The method of claim 1, wherein the location of the known defect of interest is obtained based on design data for the wafer.

4. The method of claim 1, wherein the location of the known defect of interest is obtained based on optical images or scanning electron microscope images of the wafer.

5. The method of claim 1, further comprising determining the location of the known defect of interest in an optical image of the wafer by correlating a scanning electron microscope image of the known defect of interest to the optical image of the wafer.

6. The method of claim 1, wherein acquiring the information for the target comprises grabbing images of the target on the wafer with multiple channels of the inspection system, and wherein the multiple channels comprise at least the first channel and the second channel.

7. The method of claim 1, wherein acquiring the information for the target comprises grabbing images of the pattern of interest with multiple channels of the inspection system, determining which of the grabbed images is best for pattern searching, and designating one of the multiple channels with which the best of the grabbed images for the pattern searching was grabbed as the first channel.

8. The method of claim 1, wherein acquiring the information for the target comprises generating additional images of the wafer at and proximate to the known defect of interest with multiple channels of the inspection system, determining which of the additional images is best for pattern searching, and selecting the pattern of interest from the additional image that is determined to be the best for the pattern searching.

9. The method of claim 1, wherein acquiring the information for the target comprises grabbing images of the known defect of interest with multiple channels of the inspection system, determining which of the grabbed images is best for said detecting, and designating one of the multiple channels with which the best of the grabbed images was grabbed as the second channel.

10. The method of claim 1, wherein acquiring the information for the target comprises specifying size, shape and location of care areas, size, shape and location of templates, and area where the one or more characteristics are determined in the images to which the one or more detection parameters are applied.

11. The method of claim 1, wherein acquiring the information for the target comprises grabbing templates for all known defects of interest in one die, on the wafer or the other wafer, in which said searching is performed with at least the first channel of the inspection system.

12. The method of claim 1, wherein acquiring the information for the target comprises determining a similarity between a template for the pattern of interest and an image of the target acquired by imaging the target on the wafer with the first channel and determining a uniqueness of the pattern of interest relative to other patterns proximate to the pattern of interest.

13. The method of claim 1, wherein the pattern of interest has a width and a height that are shorter than a width and a height, respectively, of dies formed on the wafer and the other wafer.

14. The method of claim 1, wherein the one or more characteristics comprise size, shape, intensity, contrast, or polarity of the known defect of interest.

15. The method of claim 1, wherein the one or more characteristics comprise one or more characteristics of the known defect of interest determined from the second image acquired with the second channel.

16. The method of claim 1, wherein the location of the known defect of interest is unique relative to the location of the pattern of interest.

17. The method of claim 1, wherein micro care areas are generated to cover one or more of the potential defect of interest locations.

18. The method of claim 1, wherein said acquiring and said searching are performed with the inspection system in a setup step before defect detection.

19. The method of claim 1, wherein said acquiring and said searching are performed with a different inspection system of the same type as the inspection system.

20. The method of claim 1, wherein said acquiring and said searching are performed in different dies on the wafer or the other wafer, and wherein said searching is performed in one die on the wafer or the other wafer using one or more templates for the target candidates.

21. The method of claim 1, further comprising determining one or more parameters of a care area based on results of said searching.

22. The method of claim 1, further comprising determining a care area location by correlating a template image for the pattern of interest and the images for the target candidates acquired by the first channel and applying the care area location to the images acquired by the second channel of the potential defect of interest locations.

23. The method of claim 1, further comprising selecting one or more characteristics of the target, selecting the one or more detection parameters, and determining one or more parameters of a care area such that defects other than the known defect of interest are not detected in the target candidates.

24. The method of claim 1, further comprising creating a template for the pattern of interest and modifying the template by changing the size of the template or flipping, rotating, or processing the template.

25. The method of claim 1, wherein the first channel, at least in part, defines the best optics mode for image matching of the images of the target candidates to the first image or a template for the pattern of interest.

26. The method of claim 1, further comprising determining the one or more detection parameters based on the information for the target.

27. The method of claim 1, wherein the inspection system uses different optics modes in the first and second channels, and wherein the different optics modes are defined by spectrum, aperture, polarization, or some combination thereof.

28. The method of claim 1, wherein the images acquired by the first and second channels are spatially registered to each other by image sensor calibration and alignment algorithms applied on the images.

29. A non-transitory computer-readable medium, storing program instructions executable on a computer system for performing a computer-implemented method for detecting defects on a wafer, wherein the computer-implemented method comprises:

acquiring information for a target on a wafer, wherein the target comprises a pattern of interest formed on the wafer and a known defect of interest occurring proximate to or in the pattern of interest, and wherein the information comprises a first image of the pattern of interest on the wafer acquired by imaging the pattern of interest on the wafer with a first channel of an inspection system, a second image of the known defect of interest on the wafer acquired by imaging the known defect of interest with a second channel of the inspection system, a location of the pattern of interest on the wafer, a location of the known defect of interest relative to the pattern of interest, and one or more characteristics computed from the pattern of interest and the known defect of interest;

searching for target candidates in one die on the wafer or on another wafer, wherein the target candidates comprise the pattern or interest; and detecting the known defect of interest in the target candidates by identifying potential defect of interest locations based on images of the target candidates acquired by the first channel and applying one or more detection parameters to images acquired by the second channel of the potential defect of interest locations.

30. A system configured to detect defects on a wafer, comprising:

an inspection subsystem configured to acquire information for a target on a wafer, wherein the target comprises a pattern of interest formed on the wafer and a known defect of interest occurring proximate to or in the pattern of interest, and wherein the information comprises a first image of the pattern of interest on the wafer acquired by imaging the pattern of interest on the wafer with a first channel of the inspection subsystem and a second image of the known defect of interest on the wafer acquired by imaging the known defect of interest with a second channel of the inspection subsystem;

wherein the inspection subsystem is further configured to search for target candidates in one die on the wafer or on another wafer, wherein the target candidates comprise the pattern of interest; and a computer system configured to detect the known defect of interest in the target candidates by identifying potential defect of interest locations based on images of the target candidates acquired by the first channel and applying one or more detection parameters to images acquired by the second channel of the potential defect of interest locations.

31. The system of claim 30, wherein design data for the wafer or the other wafer is not required for any step performed by the inspection subsystem or the computer system.

32. The system of claim 30, wherein a location of the known defect of interest is obtained based on design data for the wafer.

33. The system of claim 30, wherein a location of the known defect of interest is obtained based on optical images or scanning electron microscope images of the wafer.

34. The system of claim 30, wherein the computer system is further configured for determining a location of the known defect of interest in an optical image of the wafer by correlating a scanning electron microscope image of the known defect of interest to the optical image of the wafer.

35. The system of claim 30, wherein the inspection subsystem is further configured to acquire the information for the target by grabbing images of the target on the wafer with multiple channels of the inspection subsystem, and wherein the multiple channels comprise at least the first channel and the second channel.

36. The system of claim 30, wherein the inspection subsystem is further configured to acquire the information for the target by grabbing images of the pattern of interest with multiple channels of the inspection subsystem, and wherein the computer system is further configured for determining which of the grabbed images is best for pattern searching and designating one of the multiple channels with which the best of the grabbed images for the pattern searching was grabbed as the first channel.

37. The system of claim 30, wherein the inspection subsystem is further configured to acquire the information for the target by generating additional images of the wafer at and proximate to the known defect of interest with multiple channels of the inspection subsystem, and wherein the computer system is further configured for determining which of the additional images is best for pattern searching and selecting the pattern of interest from the additional image that is determined to be the best for the pattern searching.

38. The system of claim 30, wherein the inspection subsystem is further configured to acquire the information for the target by grabbing images of the known defect of interest with multiple channels of the inspection subsystem, and wherein the computer system is further configured for determining which of the grabbed images is best for detecting the known defect of interest and designating one of the multiple channels with which the best of the grabbed images was grabbed as the second channel.

39. The system of claim 30, wherein the computer system is further configured to acquire the information for the target by specifying size, shape and location of care areas, size, shape and location of templates, and area where one or more characteristics are determined in the images to which the one or more detection parameters are applied.

40. The system of claim 30, wherein the inspection subsystem is further configured to acquire the information for the target by grabbing templates for all known defects of interest in one die, on the wafer or the other wafer, in which the inspection subsystem searches for the target candidates with at least the first channel of the inspection subsystem.

41. The system of claim 30, wherein the computer system is further configured for acquiring the information for the target by determining a similarity between a template for the pattern of interest and an image of the target acquired by imaging the target on the wafer with the first channel and determining a uniqueness of the pattern of interest relative to other patterns proximate to the pattern of interest.

42. The system of claim 30, wherein the pattern of interest has a width and a height that are shorter than a width and a height, respectively, of dies formed on the wafer and the other wafer.

43. The system of claim 30, wherein the information for the target further comprises one or more characteristics computed from the pattern of interest and the known defect of interest, and wherein the one or more characteristics comprise size, shape, intensity, contrast, or polarity of the known defect of interest.

44. The system of claim 30, wherein the information for the target further comprises one or more characteristics computed from the pattern of interest and the known defect of interest, and wherein the one or more characteristics comprise one or more characteristics of the known defect of interest determined from the second image acquired with the second channel.

45. The system of claim 30, wherein a location of the known defect of interest is unique relative to a location of the pattern of interest.

46. The system of claim 30, wherein micro care areas are generated to cover one or more of the potential defect of interest locations.

47. The system of claim 30, wherein the inspection subsystem is further configured to acquire the information and search for the target candidates in a setup step before defect detection.

48. The system of claim 30, wherein the inspection subsystem is further configured to acquire the information and search for the target candidates in different dies on the wafer or the other wafer, and wherein the inspection subsystem is further configured to search for the target candidates in one die on the wafer or the other wafer using one or more templates for the target candidates, 49. The system of claim 30, wherein the computer system is further configured for determining one or more parameters of a care area based on results of searching for the target candidates.

50. The system of claim 30, wherein the computer system is further configured for determining a care area location by correlating a template image for the pattern of interest and the images for the target candidates acquired by the first channel and applying the care area location to the images acquired by the second channel of the potential defect of interest locations.

51. The system of claim 30, wherein the computer system is further configured for selecting one or more characteristics of the target, selecting the one or more detection parameters, and determining one or more parameters of a care area such that defects other than the known defect of interest are not detected in the target candidates.

52. The system of claim 30, wherein the computer system is further configured for creating a template for the pattern of interest and modifying the template by changing the size of the template or flipping, rotating, or processing the template.

53. The system of claim 30, wherein the first channel, at least in part, defines the best optics mode for image matching of the images of the target candidates to the first image or a template for the pattern of interest.

54. The system of claim 30, wherein the computer system is further configured for determining the one or more detection parameters based on the information for the target.

55. The system of claim 30, wherein the inspection subsystem uses different optics modes in the first and second channels, and wherein the different optics modes are defined by spectrum, aperture, polarization, or some combination thereof.

56. The system of claim 30, wherein the images acquired by the first and second channels are spatially registered to each other by image sensor calibration and alignment algorithms applied on the images.

* * * * *